US010125117B2

(12) United States Patent
Stojanovic et al.

(10) Patent No.: US 10,125,117 B2
(45) Date of Patent: Nov. 13, 2018

(54) ACTIVATION OR REACTIVATION OF ACHE

(71) Applicant: The Trustees of Columbia University in the City of New York, New York, NY (US)

(72) Inventors: Milan Stojanovic, Fort Lee, NJ (US); Francine Katz, New York, NY (US); Donald W. Landry, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/800,194

(22) Filed: Jul. 15, 2015

(65) Prior Publication Data
US 2016/0031854 A1 Feb. 4, 2016

Related U.S. Application Data

(63) Continuation-in-part of application No. PCT/US2014/044116, filed on Jun. 25, 2014, which is a continuation-in-part of application No. PCT/US2014/011720, filed on Jan. 15, 2014.

(60) Provisional application No. 61/839,280, filed on Jun. 25, 2013, provisional application No. 61/752,940, filed on Jan. 15, 2013.

(51) Int. Cl.
*C07D 401/12* (2006.01)
*C07D 233/60* (2006.01)
*C07D 215/44* (2006.01)

(52) U.S. Cl.
CPC ......... *C07D 401/12* (2013.01); *C07D 215/44* (2013.01); *C07D 233/60* (2013.01)

(58) Field of Classification Search
CPC ... C07D 401/12; C07D 223/60; C07D 215/44
See application file for complete search history.

(56) References Cited

U.S. PATENT DOCUMENTS

| | | | |
|---|---|---|---|
| 4,806,537 A | 2/1989 | Roberts | |
| 5,695,750 A | 12/1997 | Doctor et al. | |
| 5,929,093 A | 7/1999 | Pang et al. | |
| 6,103,749 A | 8/2000 | Cavalla et al. | |
| 6,784,194 B2 | 8/2004 | Lallement et al. | |
| 7,348,403 B2 | 3/2008 | Landry et al. | |
| 7,598,199 B2 | 10/2009 | Hatton et al. | |
| 8,222,297 B2 * | 7/2012 | Su | C07C 275/42 514/597 |
| 8,642,660 B2 * | 2/2014 | Goldfarb | A61K 31/122 514/18.9 |
| 9,512,082 B2 * | 12/2016 | Buchholz | C07D 233/61 |
| 2005/0260291 A1 | 11/2005 | Palu et al. | |
| 2007/0160700 A1 | 7/2007 | Palu et al. | |
| 2009/0098200 A1 | 4/2009 | Temtsin Krayz et al. | |
| 2011/0065104 A1 | 3/2011 | Landry et al. | |
| 2012/0196882 A1 | 8/2012 | Raj et al. | |
| 2012/0237957 A1 | 9/2012 | Lee | |
| 2013/0035351 A1 | 2/2013 | McHardy et al. | |

FOREIGN PATENT DOCUMENTS

| | | |
|---|---|---|
| EP | 0606366 | 7/1994 |
| WO | WO 1991/000858 | 1/1991 |
| WO | WO 1993/006105 | 4/1993 |
| WO | WO 2006/076024 | 7/2006 |
| WO | WO 2006/103120 | 10/2006 |
| WO | WO 2006/137052 | 12/2006 |
| WO | WO 2008/020302 | 2/2008 |
| WO | WO 2008/086452 | 7/2008 |
| WO | WO 2011/142826 | 11/2011 |
| WO | WO 2012/122405 | 9/2012 |
| WO | WO 2014/113495 | 7/2014 |

OTHER PUBLICATIONS

Ribeiro, J Braz Chem Soc, vol. 23(7), 1216-1225, 2012.*
Perkins, Inhalation TOxicology, vol. 24(9), 539-549, 2012.*
Janz, J Org Chem, vol. 74, 8874-8877, 2009. (Year: 2009).*
Kakadiya, Biorg&Med Chem, 18, 2285-2299. 2010. (Year: 2010).*
Atanasov et al., In vitro investigation of efficacy of new reactivators on OPC inhibited rat brain acetylcholinesterase, Chem Biol Interact., 2013, vol. 203, No. 1, pp. 139-143.
Barelli et al., New experimental Oximes in the management of organophosphorus pesticides poisoning, Minerva Anestesiologica, 2011, vol. 77, No. 12, pp. 1197-1203.
Bedford et al., Structure-Activity Relationships for Reactivators of Organophosphorus-Inhibited Acetylcholinesterase: Quaternary Salts of 2-[(hydroxyimino)methyl]imidazole, J Med Chem., 1984, vol. 27, No. 11, pp. 1431-1438.
Centers for Disease Control and Prevention, Facts About Sarin, downloaded from the internet at http://www.bt.cdc.gov/agent/sarin/basics/facts.asp on Feb. 11, 2016, 2 pages.
Centers for Disease Control and Prevention, Facts about Vx, downloaded from the internet at http://emergency.cdc.gov/agent/vx/basics/facts.asp on Feb. 11, 2016.
Chambers et al., Testing of novel brain-penetrating oxime reactivators of acetylcholinesterase inhibited by nerve agent surrogates, Chem Biol Interact., 2013, vol. 203, No. 1, pp. 135-138.
Dillon et al., RNAi as an Experimental and Therapeutic Tool to Study and Regulate Physiological and Disease Processes, Annual Review of Physiology, 2005, vol. 67, pp. 147-173.
Dykzhoorn et al., The Silent Revolution: RNA Interference as Basic Biology, Research Tool, and Therapeutic, Annual Review of Medicine, 2005, vol. 56, pp. 401-423.

(Continued)

*Primary Examiner* — D Margaret M Seaman
(74) *Attorney, Agent, or Firm* — Dentons US LLP

(57) ABSTRACT

Disclosed herein is an in vitro or in vivo method of activating or reversing inactivation of acetylcholinesterase (AChE) or butyrylcholinesterase (BuchE) using compounds of the present disclosure. Also disclosed is a method of treating a subject exposed to a nerve agent using such compounds. Also disclosed is a method of treating organophosphate poisoning in a subject using such compounds. Also disclosed is a method of modulating neuronal signaling and transmission in a subject using such compounds.

8 Claims, 30 Drawing Sheets

(56) References Cited

OTHER PUBLICATIONS

Elhai et al., Conjugal Transfer of DNA to Cyanobacteria, Methods in Enzymology, 1988, vol. 167, pp. 747-754.
Fanning et al., Gene-Expressed RNA as a Therapeutic: Issues to Consider Using Ribozymes and Small Hairpin RNA as Specific Examples, Handb Exp Pharmacol., 2006, vol. 173, pp. 289-303.
Fontaine et al., A study of the Effects of Amodiaquine on the Guinea-Pig Isolated Ileum, 1980, Naunyn-Schmiedeberg's Arch Pharmacol., vol. 313, pp. 165-170.
Ghadessy et al., Directed evolution of polymerase function by compartmentalized self-replication, Proc Natl Acad Sci USA, 2001, vol. 98, No. 8, pp. 4552-4557.
Helene et al., Control of Gene Expression by Triple Helix-Forming Oligonucleotides, Annals New York Academy of Sciences, 1992, vol. 660, pp. 27-36.
Holstege et al., Insecticides, Current Treatment Options in Neurology, 2004, vol. 6, No. 1, pp. 17-23.
Hornick et al., The Coumarin Scopoletin Potentiates Acetylcholine Release from Synaptosomes, Amplifies Hippocampal Long-Term Potentiation and Ameliorates Anticholinergic- and Age-Impaired Memory, Neuroscience, 2011, vol. 197, pp. 280-292.
International Search Report and Written Opinion dated May 6, 2014 in related International Application No. PCT/US2014/011720, 5 pages.
International Search Report and Written Opinion dated Oct. 15, 2014 in related International Application No. PCT/US2014/044116, 5 pages.
Irwin et al., Zinc—A Free Database of Commercially Available Compounds for Virtual Screening, J Chem Inf Model., 2005, vol. 45, No. 1, pp. 177-182.
Jun et al., In Vitro Ability of Currently Available Oximes to Reactivate Organophosphate Pesticide-Inhibited Human Acetylcholinesterase and Butyrylcholinesterase, International Journal of Molecular Sciences, 2011, vol. 12, No. 3, pp. 2077-2087.
Kuca et al., Structural Requirements of Acetylcholinesterase Reactivators, Mini-Reviews in Medicinal Chemistry, 2006, vol. 6, No. 3, pp. 269-277.
Lee et al., Aptamer therapeutics advance, Current Opinions in Chemical Biology, 2006, vol. 10, pp. 282-289.
Link et al., Beyond toothpicks: new methods for isolating mutant bacteria, Nature Reviews, 2007, vol. 5, pp. 680-688.
LIOFILCHEM®, MAIA Pesticide MultiTest, downloaded from the internet at http://liofilchem.net/en/maia.php on Jul. 26, 2012, 2 pages.
Lipinski, Drug-like properties and the causes of poor solubility and poor permeability, Journal of Pharmacological and Toxicological Methods, 2000, vol. 44, pp. 235-249.
Maher, DNA Triple-Helix Formation: An Approach to Artificial Gene Repressors?, Bioassays, 1992, vol. 14, No. 12, pp. 807-815.
Mercey et al., Reactivators of Acetylcholinesterase Inhibited by Organophosphorus Nerve Agents, Accounts of Chemical Research, 2012, vol. 45, No. 5, pp. 756-766.
Millard et al., Anticholinesterases: Medical Applications of Neurochemical Principles, Journal of Neurochemistry, 1995, vol. 64, No. 5, pp. 1909-1918.
Pope, et al., Pharmacology and toxicology of cholinesterase inhibitors: uses and misuses of a common mechanism of action, Environmental Toxicology and Pharmacology, 2005, vol. 19, pp. 433-446.
Prado et al., Regulation of cholinergic activity by the vesicular acetylcholine transporter, Biochem J., 2013, vol. 450, pp. 265-274.
Pubchem, Compound Summary for CID-2862684, create date Jul. 29, 2005, 3 pages.
Pushparaj et al., Short Interfering RNA (siRNA) as a Novel Therapeutic, Clinical and Experimental Pharmacology and Physiology, 2006, vol. 33, pp. 504-510.
Radić et al., Mechanism of Interaction of Novel Uncharged, Centrally Active Reactivators with OP-hAChE Conjugates, Chem Biol Interact., 2013, vol. 203, No. 1, pp. 67-71.
Reynolds et al., Rational siRNA design for RNA interference, Nature Biotechnology, 2004, vol. 22, No. 3, pp. 326-330.
Sagner et al., Rapid filter assay for the detection of DNA polymerase activity: direct identification of the gene for the DNA polymerase from *Thermus aquaticus*, Gene, 1991, vol. 97, pp. 119-123.
Simkhada et al., Pralidoxime in Organophosphorus Poisoning, J Nepal Med Assoc., 2010, vol. 50, No. 180, pp. 300-302.
Studier, Protein production by auto-induction in high-density shaking cultures, Protein Expression & Purification, 2005, vol. 41, pp. 207-234.
Teague et al., The Design of Leadlike Combinatorial Libraries, Angew. Chem. Int. Ed., 1999, vol. 38, No. 24, pp. 3943-3948.
World Health Organization, The World Health Report 2003—Shaping the Future, 2003, 204 pages.
World Health Organization, The Impact of Pesticides on Health: Preventing Intentional and Unintentional Deaths from Pesticide Poisoning, 2004, 1 page.
Worek et al., Reactivation of organophosphate-inhibited human acetylcholinesterase by isonitrosoacetone (MINA): a kinetic analysis, Chemico-Biological Interactions, 2011, vol. 194, pp. 91-96.

\* cited by examiner

FIG. 4A-4B
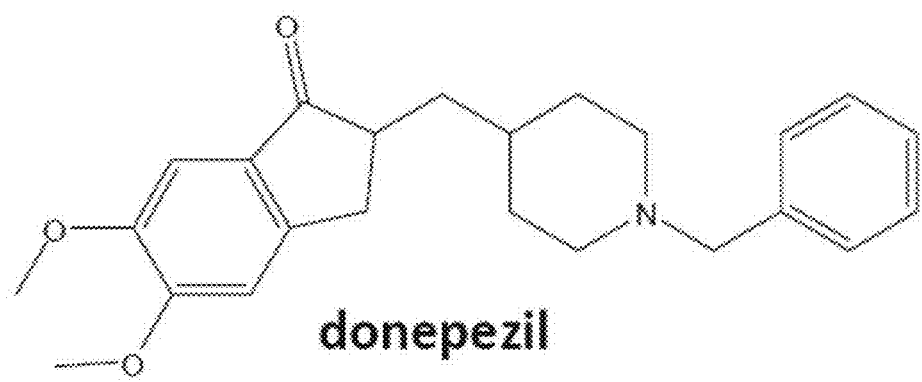
FIG. 4A
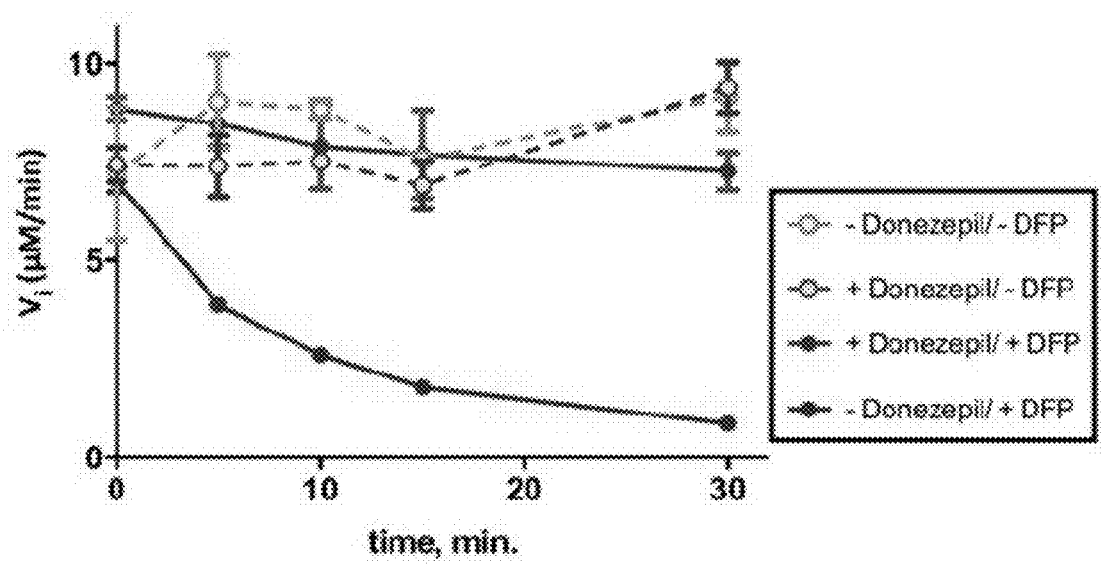
FIG. 4B

FIG. 5A
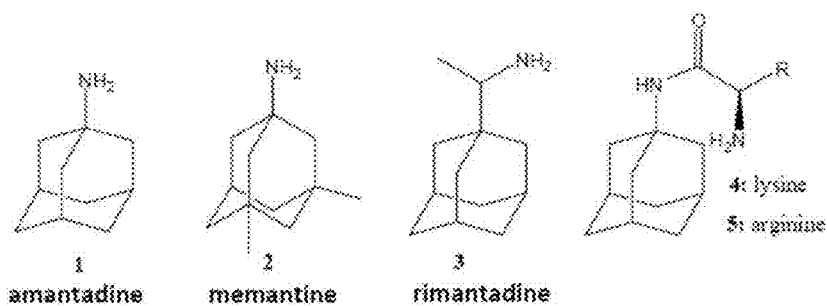
1 amantadine    2 memantine    3 rimantadine    4: lysine / 5: arginine
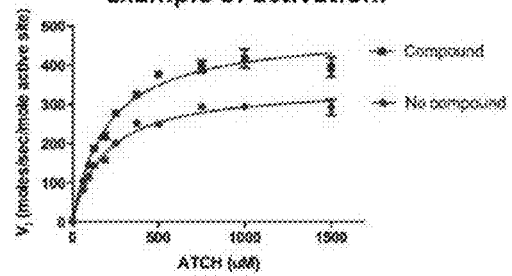
FIG. 5B
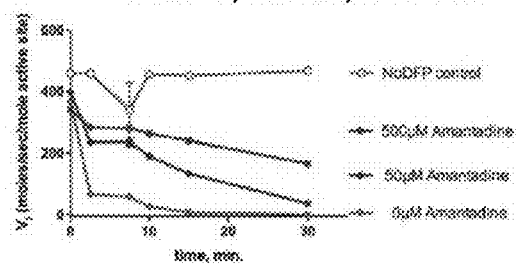
FIG. 5C

FIG. 7A 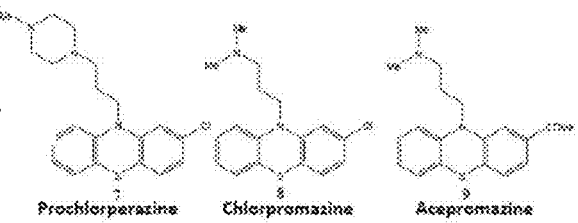 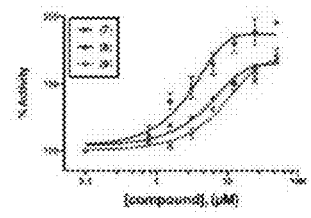
FIG. 7B 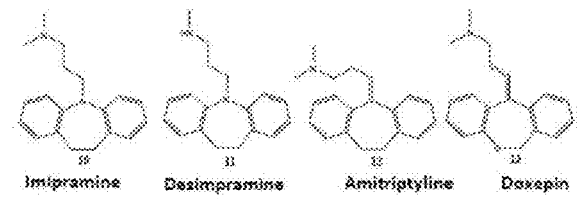 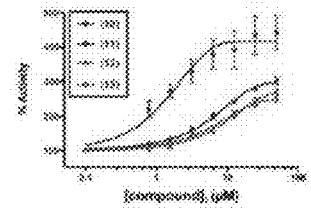
FIG. 7C 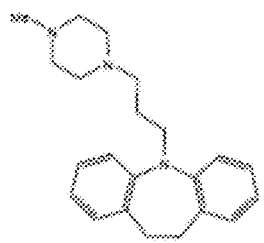 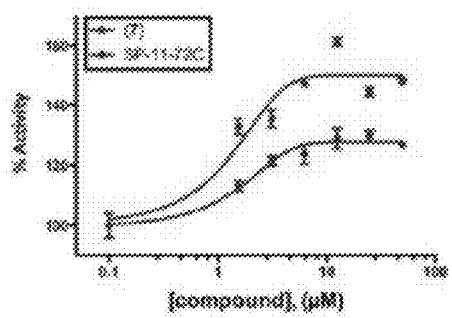
5-[3-(4-Methyl-piperazine-1-yl)-
propyl]-10,11-dihydro-5H-dibenzo[b,f]azepeine

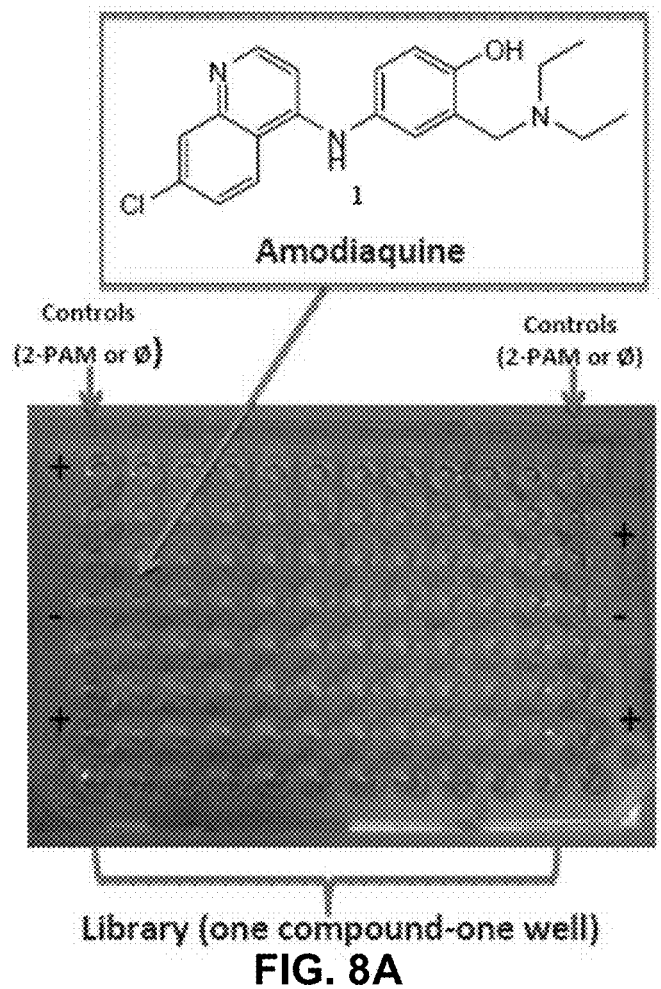
FIG. 8A
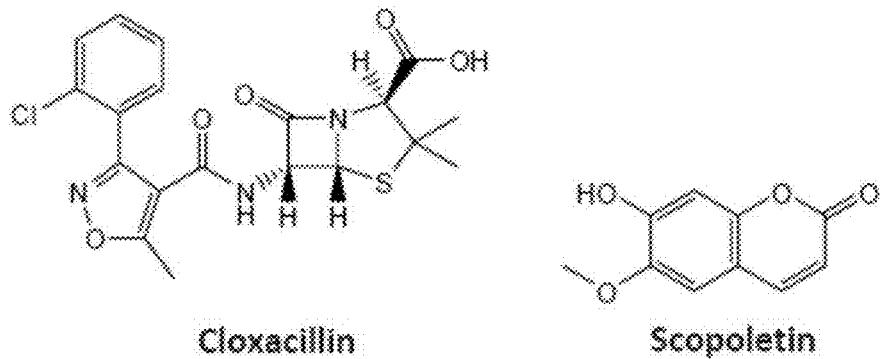
Cloxacillin
FIG. 8B
Scopoletin
FIG. 8C

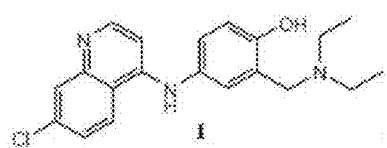
amodiaquine
FIG. 9A
chloroquine
FIG. 9B
Desethyl-amodiaquine
FIG. 9C
Dose-dependent reactivation of DiPF-inhibited AChE ("active protection"):
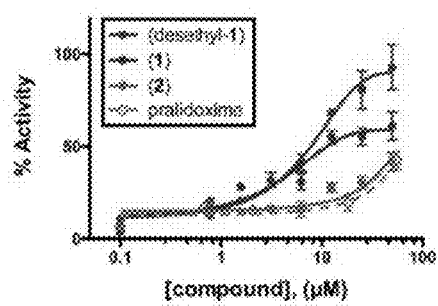
FIG. 9D
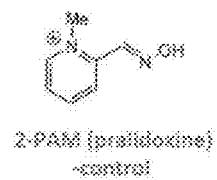
2-PAM (pralidoxime) -control
FIG. 9E

Scopoletin

Dose-dependent reactivation of paraoxon-inhibited AChE ("active protection"):

[compound], (µM)

2-PAM (pralidoxine) -control

FIG. 12A  FIG. 12B  FIG. 12C
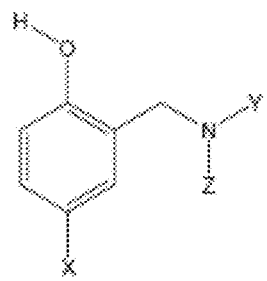
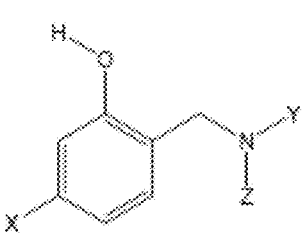
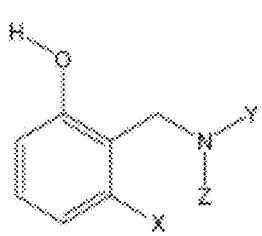
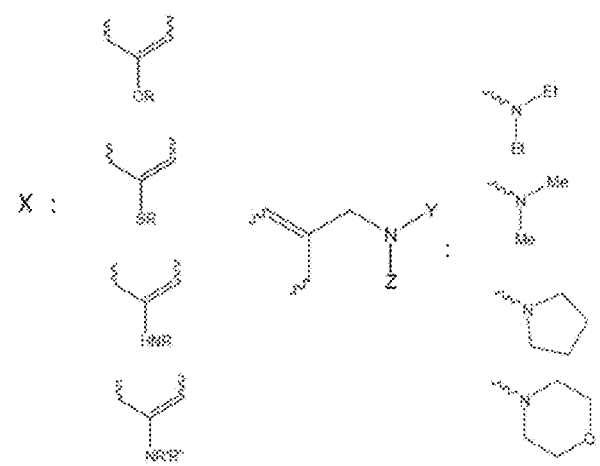
R' and R": H, alkyl, aryl, etc.   FIG. 12E
Q: NMe, O
FIG. 12D

Q: NMe, O
Y: O, HN, R'N, (O)NR', (O)S, (O)2S

Y: O, HN, R'N, (O)NR', (O)S, (O)2S

R' and R": H, alkyl, aryl, etc.

Y: O, HN, R'N, (O)NR', (O)S, (O)2S

R' and R": H, alkyl, aryl, etc.

A
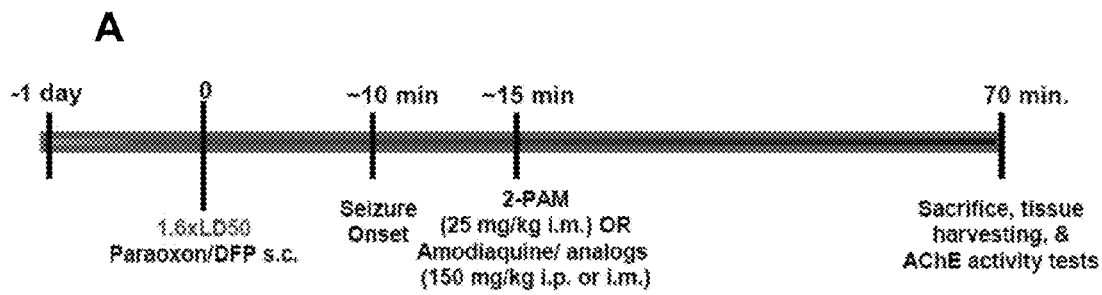
B
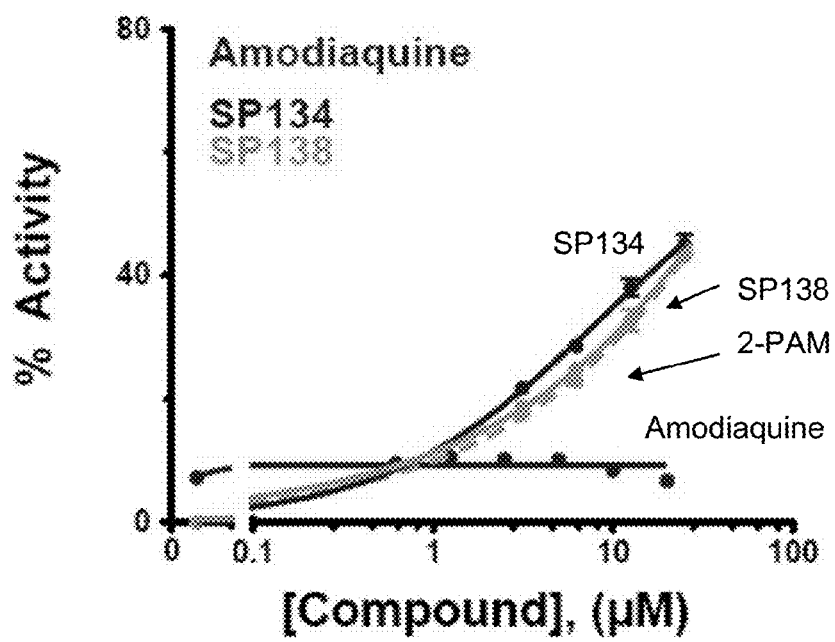
FIG. 19A
FIG. 19B

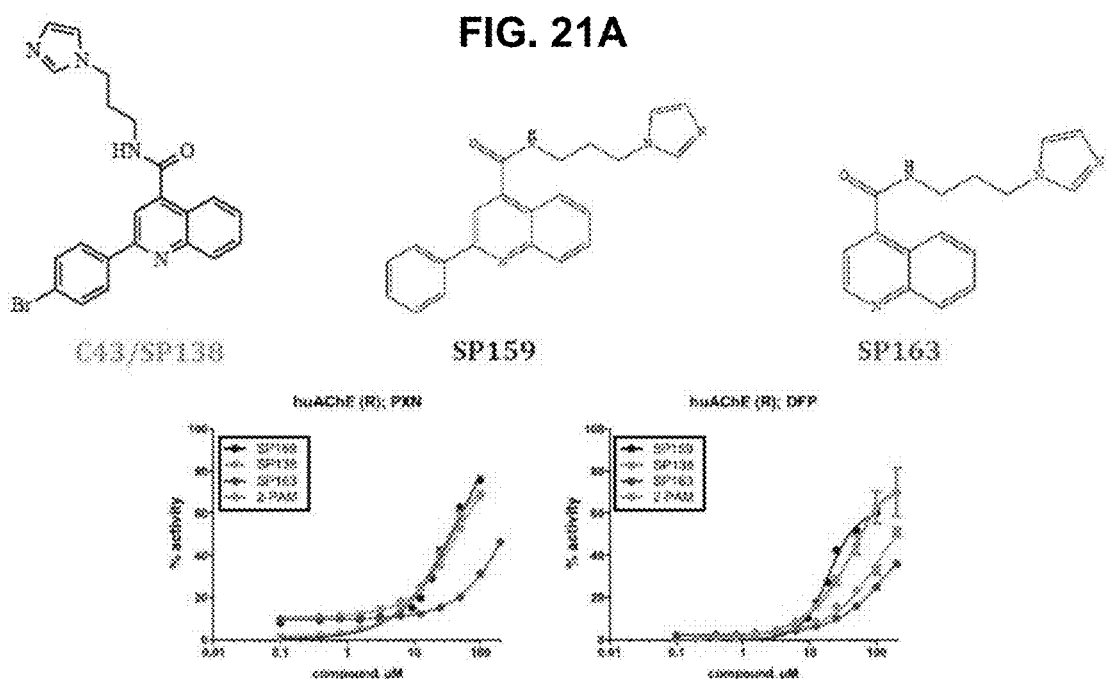

FIG. 22A
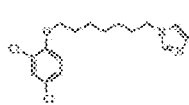 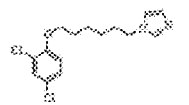 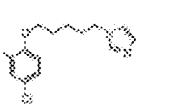  
SP135  SP120  SP134  SP123  SP130
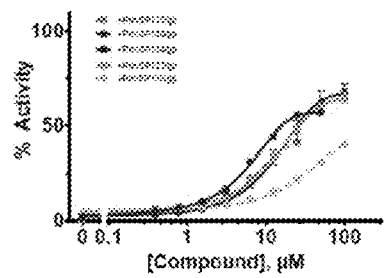 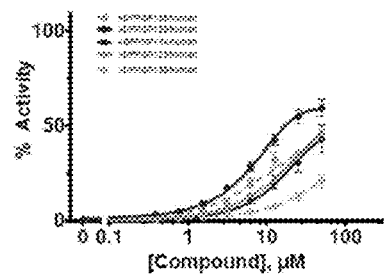
FIG. 22B  FIG. 22C

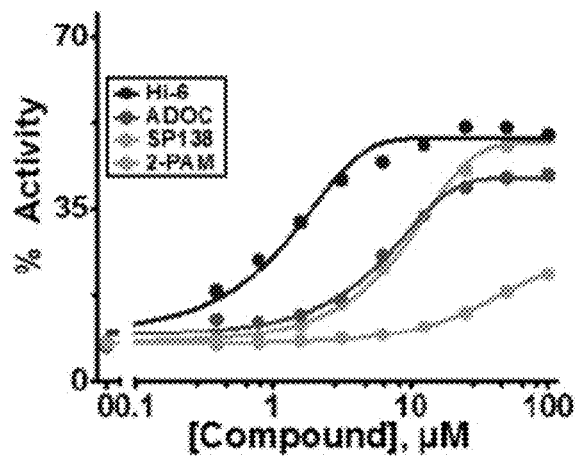
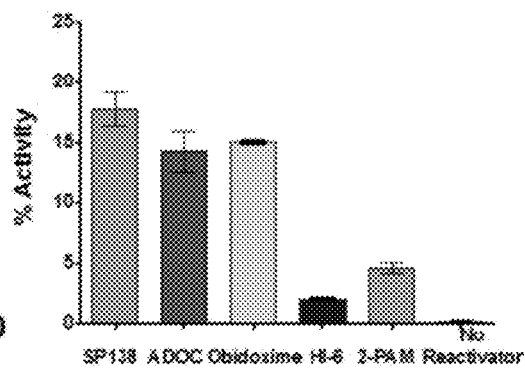
FIG. 24A
FIG. 24B
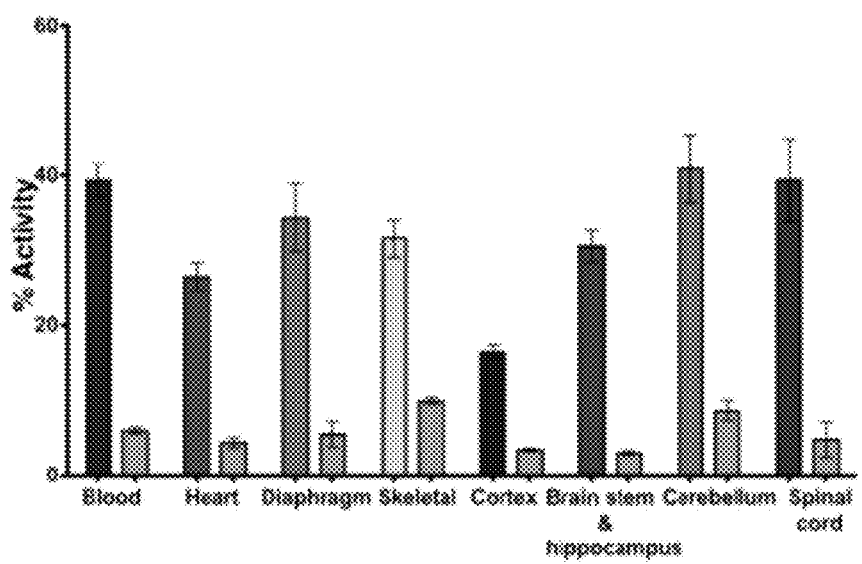
FIG. 24C

ACTIVATION OR REACTIVATION OF ACHE

CROSS-REFERENCE TO RELATED APPLICATIONS

The present application is a Continuation in Part of (1) International Application No. PCT/US14/44116 filed 25 Jun. 2014, which claims the benefit of International Application No. PCT/US14/11720 filed 15 Jan. 2014 and U.S. Provisional Application Ser. No. 61/839,280 filed 25 Jun. 2013; and (2) International Application No. PCT/US14/11720 filed 15 Jan. 2015, which claims the benefit of U.S. Provisional Application Ser. No. 61/839,280 filed 25 Jun. 2013 and U.S. Provisional Application Ser. No. 61/752,940 filed 15 Jan. 2013; each of which is incorporated herein by reference in its entirety.

STATEMENT REGARDING FEDERALLY SPONSORED RESEARCH OR DEVELOPMENT

This invention was made with Government support under Grant No. CB11-MEDCHEM1-2-0005 awarded by Defense Threat Reduction Agency. The Government has certain rights in the invention.

BACKGROUND OF THE INVENTION

Acetylcholine (ACh) is a neurotransmitter present at the neuromuscular junction and at many synapses in the central nervous system. Acetylcholinesterase (AchE) is a hydrolase that hydrolyzes the neurotransmitter acetylcholine. AChE inhibitors are used as pesticides or warfare agents. These inhibitors can cause an accumulation of ACh, which can lead to over-stimulation of cholinergic receptors. Poisoning by AChE inhibitors can damage both the central and peripheral nervous systems, and can lead to death. AChE inhibitor exposure is usually treated with a combination of anticholinergic drugs and AChE re-activators.

AChE has been immobilized on biosensors, using electrodes to monitor AChE activity. MAIA Pesticide MultiTest uses a different technique to immobilize AChE.

Therapeutic agents currently available do not operate effectively. Current medical management guidelines for treatment of both nerve agent exposure and accidental organophosphate poisonings (e.g., pesticides) are administration of oxime reactivators (e.g., pralidoxine, 2-PAM) usually in conjunction with atropine. But use of oxime reactivation is limited because of the lack of blood-brain barrier penetration; necessary in vitro concentrations than cannot be obtained; and oxime adducts can be toxic.

SUMMARY OF THE INVENTION

One embodiment provides a method of activating, reactivating, or reversing inactivation of acetylcholinesterase (AChE) or butyrylcholinesterase (BuChE) including contacting, in vitro or in vivo, non-activated acetylcholinesterase or inactivated acetylcholinesterase or inactivated butyrylcholinesterase and a compound of the present disclosure.

Another embodiment provides a method of treating a subject exposed to a nerve agent including administering a compound of the present disclosure to the subject, where the compound can activate, reactivate, or reverse inactivation of acetylcholinesterase or butyrylcholinesterase.

Another embodiment provides a method of treating organophosphate poisoning in a subject including administering a compound of the present disclosure to the subject, where the compound can activate, reactivate, or reverse inactivation of acetylcholinesterase or butyrylcholinesterase.

Another embodiment provides a method of modulating neuronal signaling and transmission including administering a compound of the present disclosure to the subject, where the compound can activate, reactivate, or reverse inactivation of acetylcholinesterase or butyrylcholinesterase.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 3A is the molecular structure of an AChE activator.
FIG. 3B is the molecular structure of an AChE activator.
FIG. 3C is the molecular structure of an AChE activator.
FIG. 3D is the molecular structure of an AChE activator.
FIG. 3E is the molecular structure of an AChE activator.
FIG. 3F is the molecular structure of an AChE activator.
FIG. 3G is the molecular structure of an AChE activator.
FIG. 3H is the molecular structure of an AChE activator.
FIG. 3I is the molecular structure of an AChE activator.
FIG. 3J is the molecular structure of an AChE activator.

FIG. 4A is the molecular structure of the inhibitor donepezil. Further details can be found in Example 4.

FIG. 4B is the activation curve on donepezil. The activation curve demonstrates that donepezil protects AChE from fluorophosphate (DFP). Further details can be found in Example 4.

FIG. 5A is a series of chemical structures of amantadine, memantine, rimatadine, lysine, and arginine. Further details can be found in Example 5.

FIG. 5B is an activity curve showing the activity of AChE was enhanced when in the presence of allosteric activators that are protectors. Further details can be found in Example 5.

FIG. 5C is a dose-dependent protection curve showing the protection at various concentrations of protector. Further details can be found in Example 5.

FIG. 7A is a series of chemical structures and activation curves of the respective chemical structures. The activity profiles characterize and compare reactivators of inhibited AChE. Further details can be found in Example 5.

FIG. 7B is a series of chemical structures and activation curves of the respective chemical structures. Further details can be found in Example 5.

FIG. 7C is a chemical structures and activation curve of the respective chemical structure and SP-11-72C and prochlorperazine (7). Further details can be found in Example 5.

FIG. 8A is a chemical structure of activator, amodiaquine and an image of a 96-well plate. The plate shows initial hit confirmation. Further details can be found in Example 6.

FIG. 8B is a chemical structure of activator, cloxacillin. Further details can be found in Example 6.

FIG. 8C is a chemical structure of activator, scopoletin. Further details can be found in Example 6.

FIG. 9A-9E is a series of chemical structures of activators and respective dose-dependent activity profiles. Further details can be found in Example 6.

FIG. 9A is a chemical structure of amodiaquine.

FIG. 9B is a chemical structure of chloroquine.

FIG. 9C is a chemical structure of desethyl-amodiaquine.

FIG. 9D are profiles showing the reactivation of paraoxon-inhibited AChE with scopoletin.

FIG. 9E is a chemical structure of pralidoxine.

FIG. 10A is a chemical structure of reactivator scopoletin.

FIG. 10B is a dose-dependent activity profile compared to oxime, pralidoxine.

FIG. 10C is a chemical structure of pralidoxine.

FIG. 11A is a series of chemical structures of activators.

FIG. 11B is the associated activity profile of compounds 5-10 at different concentrations.

FIG. 12A-12E are a series of chemical structures of nucleophilic phenol compounds that reactivate AChE. Further details can be found in Example 7.

FIG. 12A is a chemical structure of a nucleophilic phenol compound.

FIG. 12B is a chemical structure of a nucleophilic phenol compound.

FIG. 12C is a chemical structure of a nucleophilic phenol compound.

FIG. 12D are a series of chemical structures of the X substituent.

FIG. 12E are a series of chemical structures of the amine substituent.

FIG. 13A is a chemical structure of a nucleophilic phenol compound.

FIG. 13B is a chemical structure of a nucleophilic phenol compound.

FIG. 13C is a series of chemical structures of the amine substituent.

FIG. 14A is a chemical structure of a nucleophilic phenol compound.

FIG. 14B is a chemical structure of a nucleophilic phenol compound.

FIG. 17A shows the structure of SP138 and the five domains of the molecules being systematically studied and two retrosynthetic routes that can be used to synthesize some of the analogs. Further details can be found in Example 10.

FIG. 17B shows the line and scatter plot depicting the survival analysis of SP138-treated mice challenged with DFP. Further details can be found in Example 10.

FIG. 17C is a bar graph depicting the reactivation of AChE activity in brain tissue after challenge with DFP relative to no-DFP control animal. Bar A represents 1×SP138 given pre-challenge (1×=0.25 mmol/kg); Bar B represents 1×SP138 given post-challenge; Bar C represents 1×SP138 pre-challenge and 1×SP138 post-challenge; and Bar D represents 30×2-PAM. Further details can be found in Example 10.

FIG. 19A-19B is a series of images and line and scatter plots showing the experimental paradigm and data describing the ex vivo reactivation of paraoxon-inhibition.

FIG. 19A is the experimental design for the ex vivo reactivation of paraoxon-inhibited guinea pig brain. Further details can be found in Example 12.

FIG. 19B is a line and scatter graph showing ex vivo reactivation of paraoxon-inhibited guinea pig brain tissue. 2-PAM activity is shown in dashed gray. Further details can be found in Example 12.

FIG. 21A is a series of chemical structures for C43/SP138, SP159, and SP163.

FIG. 21B is the corresponding activity profile for C43/SP138, SP159, and SP163. Further details can be found in Example 13.

FIG. 21C is the corresponding activity profile for C43/SP138, SP159, and SP163. Further details can be found in Example 13.

FIG. 22A is a series of chemical structures of SP135, SP120, SP134, SP123, and SP130.

FIG. 22B is activity profiles for SP135, SP120, SP134, SP123, and SP130. Further details can be found in Example 13.

FIG. 22C is activity profiles for SP135, SP120, SP134, SP123, and SP130. Further details can be found in Example 13.

FIG. 23A shows reactivation by ADQ of mouse PO-inhibited AChE is better than for human analog (results after three hours at indicated concentrations).

FIG. 23B shows kr2 determination for 2-PAM, HI-6, ADQ, and ADOC (at concentrations below saturation on hu-AChE), showing that amodiaquine and ADOC are faster. ADQ and ADOC have similar kr2 values (nearly parallel slopes).

FIG. 23C shows s-shaped ADOC activity vs concentration curves on a linear scale (human enzyme), consistent with second molecule of ADOC binding and enhancing reactivation. ADQ, as "anchored" ADOC, does not show this effect.

FIG. 23D shows inhibition of AChE activity by ADQ, ADOC, and SP138, where such inhibition is reversible and significant reactivation of organophosphate-inactivation of AChE occurs below inhibitory concentrations of ADQ, ADOC, or SP138.

FIG. 24A-24C are a series of line and scatter plots and bar graphs showing reactivation of huAChE.

FIG. 24A shows reactivation by Hi-6, ADOC, SP138, and 2-PAM of huAChE adduct with SIMP.

FIG. 24B shows reactivation efficacy of Hi-6, ADOC, SP138, and 2-PAM with DFP-adduct at 40 µM and three hours.

FIG. 24C shows reactivation across various tissues with ADOQ injected 20 minutes prior and 5 minutes post lethal DFP exposure. Last four bars are cortex, brain stem and hippocampus, cerebellum, and spinal cord. Matching negative controls (no ADOQ) are shown as well (gray bars). Error bars show SEM of six measurements.

FIG. 25A shows reactivation rate constants for SP138 and 2-PAM against DFP-inhibited AChE. SP138 (10.7 $M^{-1}$ $min^{-1}$) has ~3-fold efficiency over 2-PAM (3.4 $M^{-1}$ $min^{-1}$).

FIG. 25B shows reactivation in various tissues from mice fed SP138 before challenge with DFP. Values of % Activity are relative to activity in untreated, unchallenged animals. Residual activity in animals challenged with DFP, but untreated with 2-PAM is shown as a gray bar for matching tissues.

FIG. 26A shows tissue activity of AChE in surviving mice pre-treated with 5 mg ADQ 24 hours after treatment with 1.6×LD50 DFP s.c.

FIG. 26B shows tissue activity of AChE in surviving mice pre-treated with 1 mg ADQ 24 hours after treatment with 1.6×LD50 DFP s.c.

FIG. 26C shows tissue activity of AChE in surviving mice pre-treated with 1 mg ADQ 24 hours after treatment with 1.6×LD50 DFP s.c.

FIG. 27A shows liver histology of a mouse treated with 120 mg/jg ADOC.

FIG. 27B shows liver histology of an untreated control mouse.

FIG. 28A shows reactivation % activity) of paraoxon inactivated huBuChE as a function of concentration of amodiaquine, #17, SP110, SP134, and 2-PAM (uM).

FIG. 28B shows reactivation % activity) of paraoxon inactivated huBuChE as a function of concentration of SP134, prochlorperazine, SP138, and 2-PAM (uM).

FIG. 28C shows reactivation % activity) of paraoxon inactivated huAChE as a function of concentration of SP134, prochlorperazine, SP138, and 2-PAM (uM).

DETAILED DESCRIPTION OF THE INVENTION

Figure 1:
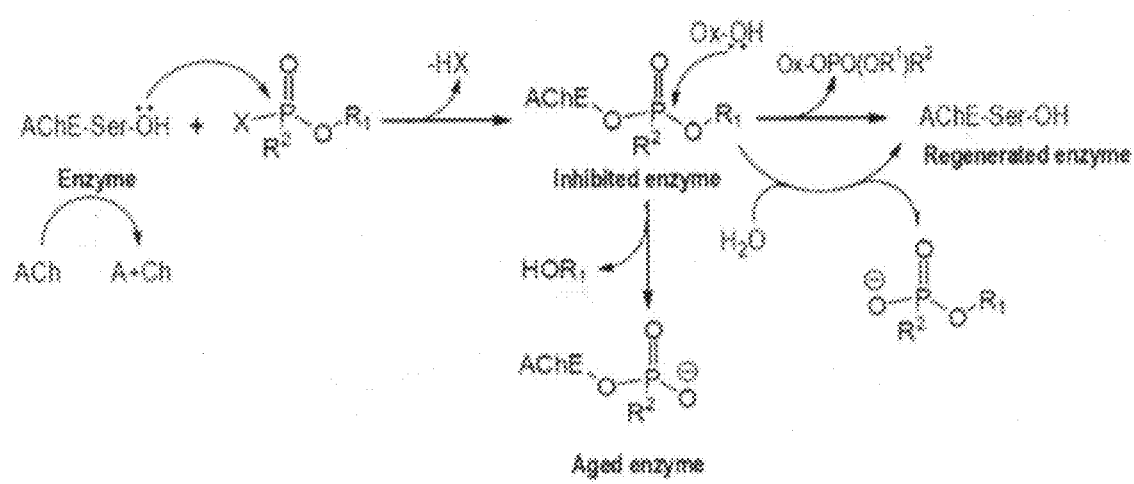
FIG. 1 is a reaction scheme depicting the inhibition of AChE, aging of the inhibited AChE, and reactivation of inhibited AChE. Further details can be found in Example 1.

The present disclosure is based at least in part on the discovery that the compound amodiaquine (an FDA approved drug) can reverse inactivation of acetylcholinesterase (AChE) at concentrations that are below standard reactivators (Ka~3 uM), where such concentrations can be achieved in vivo. As shown herein, amodiaquine and derivatives and related compounds thereto can be used to treat or reverse exposure to nerve agents. Thus is provided compounds useful for treatment of nerve agent exposure or accidental organophosphate poisonings that can operate according to a different mechanism of action compared to conventional drugs for the same indication, at a lower dosage compared to conventional drugs for the same indication, or with an ability to cross the blood-brain barrier, which certain conventional drugs for the same indication cannot do.

Furthermore, compounds and methods described herein can be used to reactivate Butyrylcholinesterase (BuchE). BuchE is a non-specific cholinesterase enzyme similar to AChE that hydrolyses many different choline esters. As shown herein, in vitro, human BuChE is also reactivated by amodiaquine and amodiaquine-like compounds, indicating an additional use for these compounds as a cofactor to a traditional bioscavenger treatment approach. Such reactivators would make a BuChE-based treatment far more cost-effective and achievable.

Compounds

As described herein, various compounds have been discovered to activate or reverse inactivation of AChE. Further discussion recites reverse inactivation of AChE but one of ordinary skill will recognize that such discussion can apply to activation of AChE as well.

For example, a compound described herein that can reverse inactivation of AChE can be selected from any compound as depicted in the Figures. As another example, a compound described herein that can reverse inactivation of AChE can be selected from any compound described in the Examples.

Further compounds are discussed below.

Amodiaquine Derivatives.

As shown herein, amodiaquine can reverse inactivation of AChE:

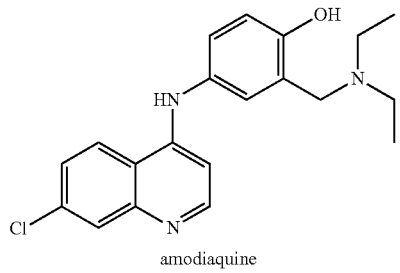

amodiaquine

But amodiaquine can have (i) insufficient solubility, making an injectable formulation for use with current auto-injectors unlikely; (ii) hydrophobic-p-aminophenol-related toxicity that led it to no longer be marketed in the USA; (iii) faster reactivation of mice and guinea pig AChE than for human, challenging the relevancy of animal results; and (iii) optimal activity occurs at concentrations that could lead to unacceptable toxicity within a civilian population exposed to agents that are not immediately lethal. Accordingly, derivatives of amodiaquine were developed as described herein.

A compound described herein can be an amodiaquine derivative. An amodiaquine derivative can have increased solubility compared to amodiaquine. An amodiaquine derivative can have decreased hydrophobicity compared to amodiaquine, which can decrease or eliminate a side effect (e.g., agranulocytosis). Exemplary amodiaquine derivatives include ADOC, SP138, SP134, and SP180, which are more soluble than amodiaquine and can achieve higher concentrations and higher levels of reactivation:

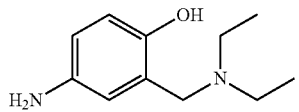

ADOC

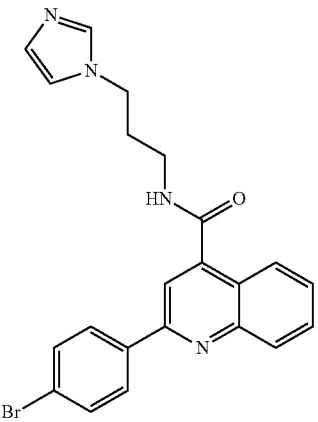

SP138

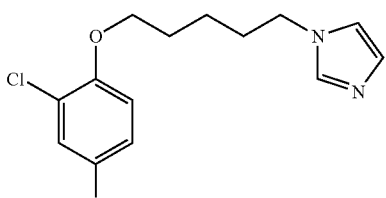

SP134

-continued

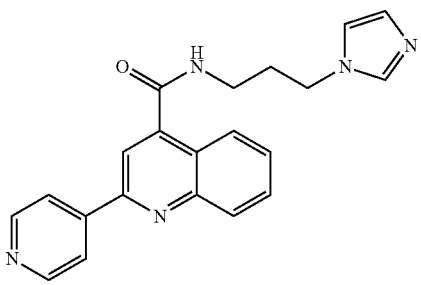

SP180

Exemplary steps leading to identification of SP138 and its analogs, starting with ADQ analog chloroquine (CQ), are depicted below.

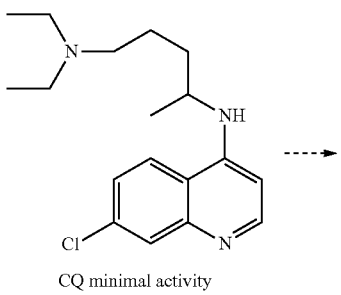

ADQ ---->

CQ minimal activity

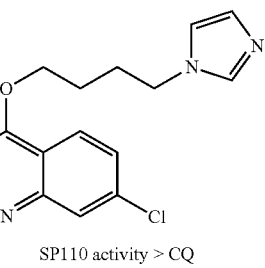

SP110 activity > CQ

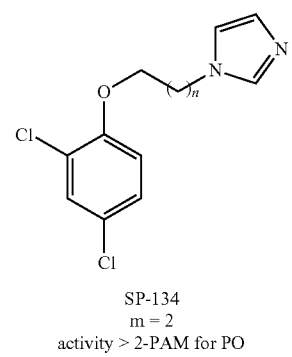

SP-134
m = 2
activity > 2-PAM for PO

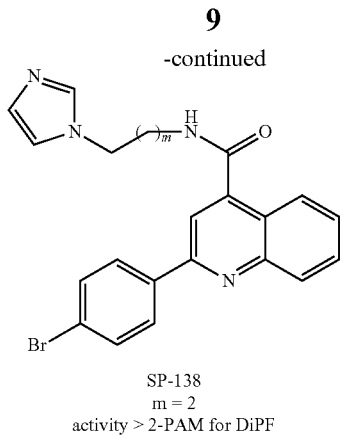

SP-138
m = 2
activity > 2-PAM for DiPF

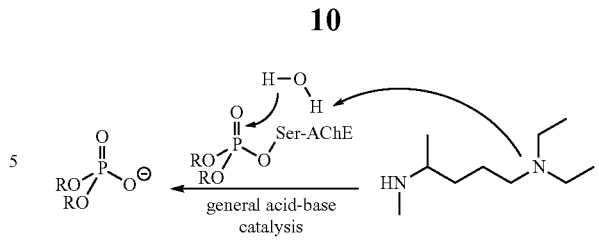

SP138 was found to be about three times (10.7 M$^{-1}$ min$^{-1}$) at DFP reactivation than 2-PAM (3.4 M$^{-1}$ min$^{-1}$) and even more so than HI-6 (0.93 M$^{-1}$ min$^{-1}$); it has a lower rate than obidoxime (38.6 M$^{-1}$ min$^{-1}$). But ADOC and SP138 reached the highest levels of reactivation than any other compound at concentrations above 40 µM, indicating they reach the highest kr (see e.g., FIG. 24B).

SP134 was found to protect against DFP lethality in vivo and also reactivates BuChE.

SP180 was found to protect against DFP lethality in vivo and is more soluble than SP138.

ADOC has much higher reactivation rates than functionally comparable 2-PAM. Allosteric effects in ADOC lead to further increase in efficacy, indicating that anchoring can be used for optimization. ADOC and analogs may not yield a toxic intermediate like oximes.

Figure 25A:
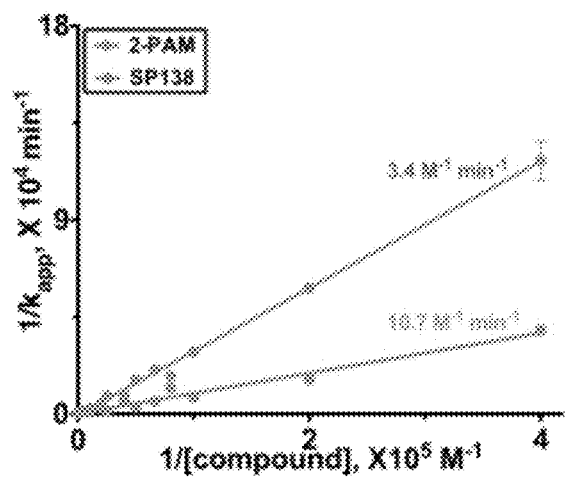
FIG. 25A-25B are a line and scatter plot and a bar graph showing reactivation of huAChE.
Figure 25B:
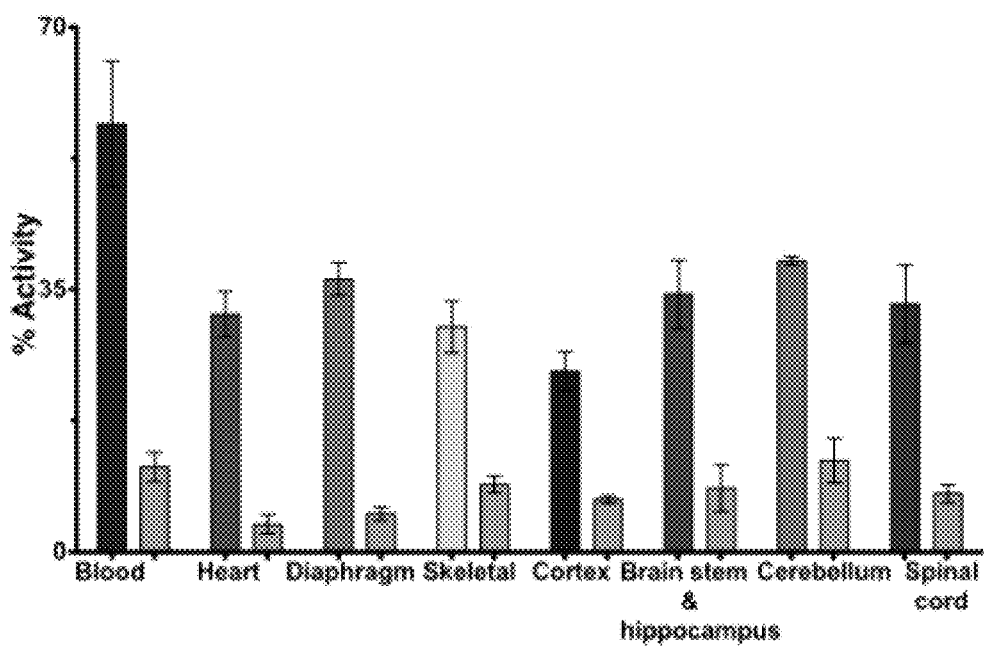

Considered in isolation and without history of their discovery, compounds described herein (e.g., SP138 and ADOC) may seem disconnected, and their related activities may have been unlikely to be predicted by any current modeling technique. But considered within the context of their discovery and the history of the research in oxime reactivators, compounds such as SP138 and ADOC are part of the same mechanistic continuum (see e.g., FIG. 25).

While under no obligation to do so, and in no way limiting the scope of the present disclosure, the following discussion of proposed mechanism is provided. It is presently thought that ADOC is a reactivating functionality providing general acid-base catalysis (with pKa around 8) and its analog in oxime research would be 2-PAM. Similarly, it is thought that SP138 is delivering an external imidazole group that provides an alternative to the native imidazole within the catalytic triad (His440), thereby enhancing spontaneous hydrolysis. Experiments have shown (e.g., comparison of amodiaquine and chloroquine) that a phenolate group is not essential for reactivation (but amodiaquine does have a higher reactivation activity than chloroquine). Because chloroquine does not have a nucleophile (e.g., as phenolate as in amodiaquine) to mediate reactivate, the mechanism is thought to be a general acid-base catalysis rather than a direct nucleophile catalysis.

A possible general acid-base catalysis mechanism is as follows (note compound is exemplary only):

The hydrophobic moiety of SP138 may anchor the imidazole close to the inhibited active site through its affinity to one of the hydrophobic/anion sites in the AChE gorge, thus, overcoming steric repulsion, increasing effective concentration, and decreasing k$_{off}$. SP138 can be viewed as a general acid/base analog of more advanced oximes. The switch from oxime to water as nucleophile may allow further flexibility in the active site leading to increases in reaction rates (e.g., any direct anchoring of nucleophile may impact unfavorably its ability to achieve favored trajectory for addition/elimination through the formation of oxyphosphorane intermediate).

A compound described herein can be a nucleophilic phenol or phenolate compound, or an analog or derivative thereof, having an ability to reverse inactivation of AChE. As another example, a compound described herein can be as shown below, or an analog or derivative thereof retaining an ability to reverse inactivation of AChE:

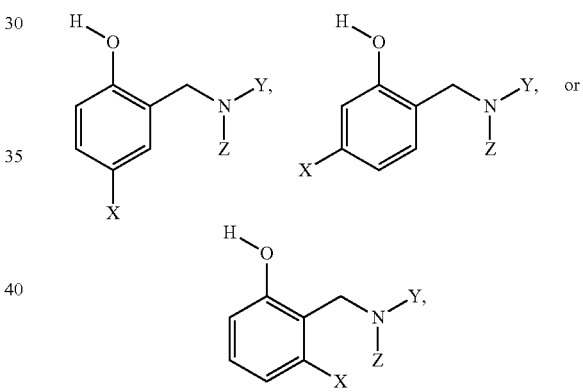

wherein
X is

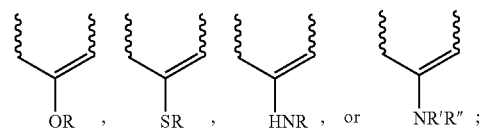

Y—N—Z of

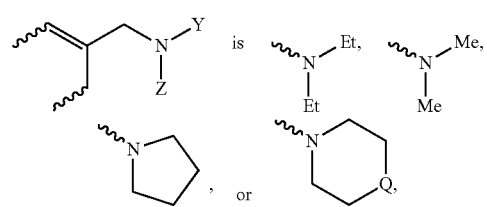

wherein R' and R" are independently selected from H, alkyl, aryl, or other similar substituents; and Q is NMe or O.

As another example, a compound described herein can be ADOC having a structure as follows:

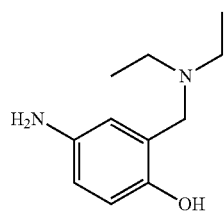

Structural comparison of ADOC to acetaminophen suggests doses could up to 200 mg/kg or more without significant negative side-effects. PAP-related toxic effects can be countered in whole or in part by co-administration of acetylcysteine with a compound described herein (e.g., ADOC).

As another example, a compound described herein can be as shown below, or an analog or derivative thereof retaining an ability to reverse inactivation of AChE:

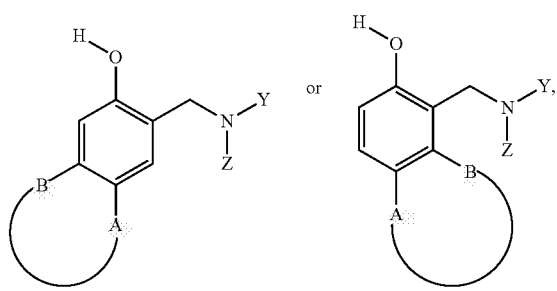

wherein substituents can be as defined herein.

As another example, a compound described herein can be as shown below, or an analog or derivative thereof retaining an ability to reverse inactivation of AChE:

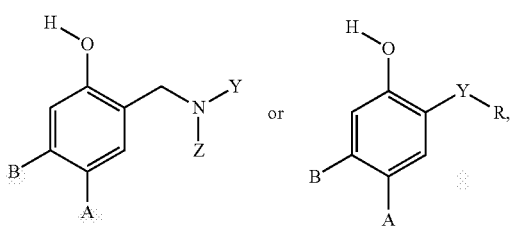

wherein Y is O, HN, R'N, (O)NR', (O)S, (O)S$_2$, or as Y is otherwise described herein; and R' and R" are independently selected from H, alkyl, aryl, or other similar substituents, or as otherwise described herein.

As another example, a compound described herein can be as shown below, or an analog or derivative thereof retaining an ability to reverse inactivation of AChE:

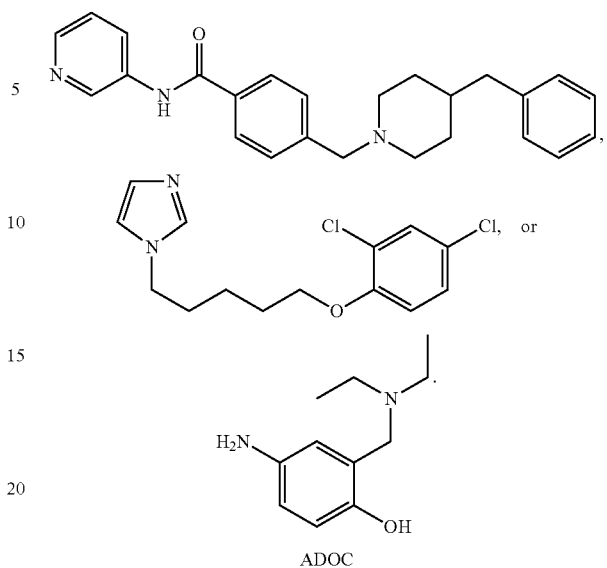

ADOC

An example of a derivative is addition of a third ring to the following compound while retaining an ability to reverse inactivation of AChE:

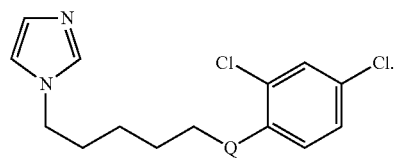

An example of a derivative is adding one or more R groups to nitrogen in the following compound (e.g., so as to mimic Aricept), retaining an ability to reverse inactivation of AChE:

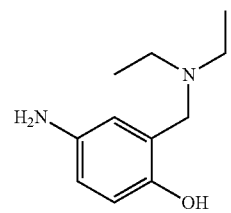

As another example, a compound described herein can be as shown below, or an analog or derivative thereof retaining an ability to reverse inactivation of AChE:

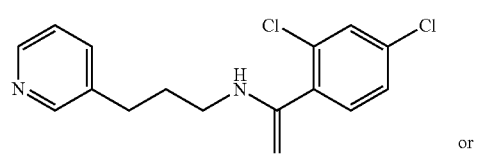

or

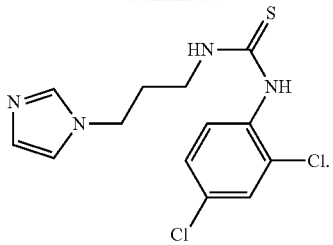

As another example, a compound described herein can be as shown below, or an analog or derivative thereof retaining an ability to reverse inactivation of AChE:

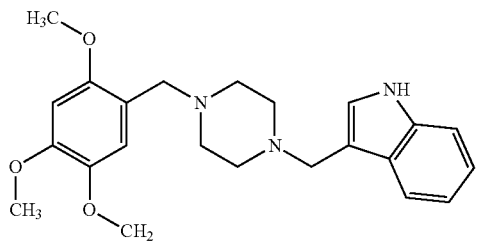

As another example, a compound described herein can be as shown below, or an analog or derivative thereof retaining an ability to reverse inactivation of AChE (e.g., an Aricept-like compound):

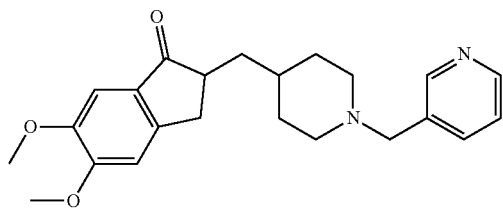

As another example, a compound described herein can be 1-Morpholinomethyl-2-napthol; 1-Piperidinomethyl-2-napthol; 2-[(dimethylamino)methyl]-4-(1,1,3,3-tetramethyl-butyl)phenol; 2,4-Bis[(dimethylamino)methyl]-6-methylphenol; 2-(4-Bromo-phenox)-3-(3-dimethylaminomethyl-2,4-dihydroxy-phenyl)-ethanone; 2-(4,5-Dihydro-1H-imidizol-2-yl)phenol; 6-(Morpholin-4-yl-(3,4,5-trimethoxy-phenyl)-methyl)-benzo(1,3)dioxol-5-ol; 2,4-Bis[(dimethylamino)methyl]-6-methylphenol; 7-Chloro-4-(4-hydroxyanilino)quinoline; 8-((Dimethylamino)me)-3-(2-fluorophenoxy)-7-hydroxy-2-methyl-4H-chromoen-4-one; or Scopoletin.

Imidazole Derivatives.

A compound described herein can be an imidazole or imidazole derivative. For example, a compound described herein can be a compound of Formula (I):

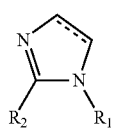

Formula (I)

or a pharmaceutically acceptable salt, including all tautomers and stereoisomers thereof.

According to Formula (I), $R_1$ can represent hydrogen or any of the following:

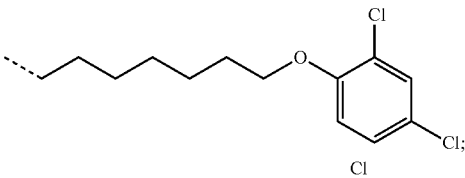

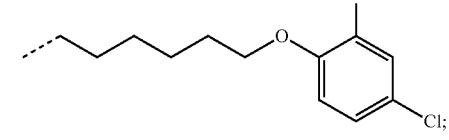

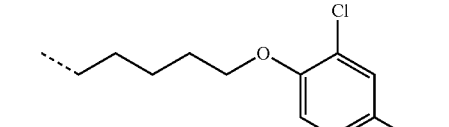

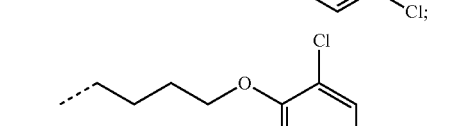

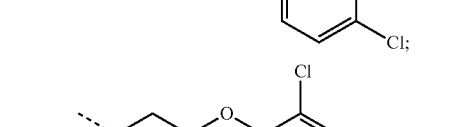

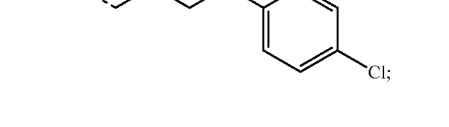

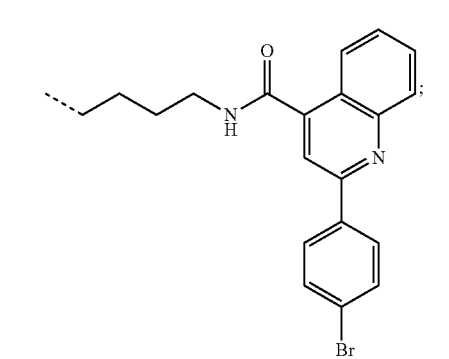

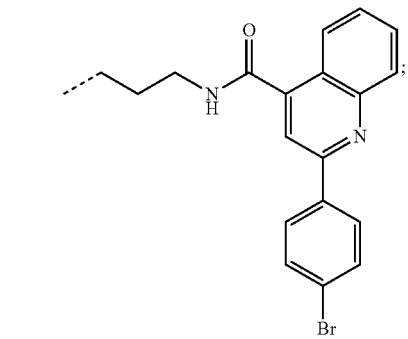

-continued

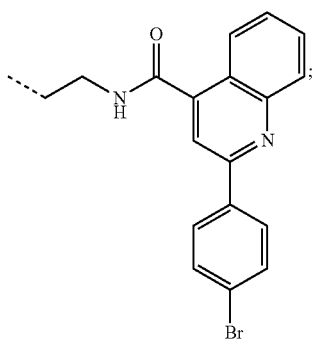

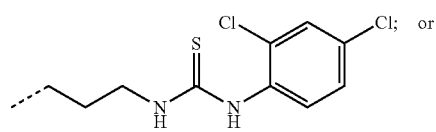

According to Formula (I), $R_2$ can represent hydrogen or

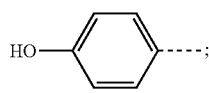

In the above structures, a dashed line (------) represents a bond and a dashed and solid line (⋯⋯) represents a double bond if $R_1$ or $R_2$ of Formula (I) is hydrogen and represents a single bond if $R_1$ and $R_2$ are not hydrogen.

As another example, a compound described herein can be

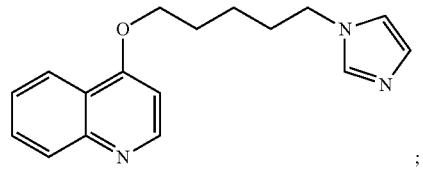

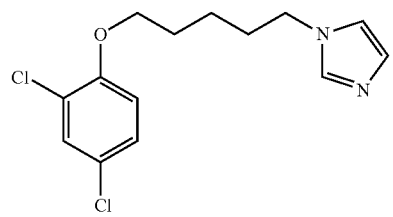

-continued

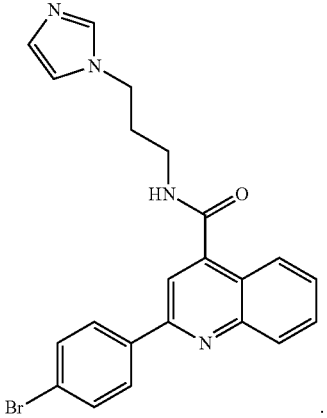

Quinoline Derivatives.

A compound described herein can be a quinoline or quinoline derivative. For example, a compound described herein can be:

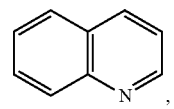

or a derivative thereof.

As another example, a compound described herein can be a compound of Formula (II):

Formula (II)

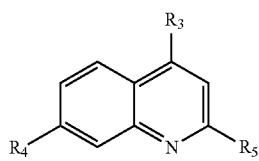

or a pharmaceutically acceptable salt, including all tautomers and stereoisomers thereof wherein.

According to Formula (II), $R_3$ can represent hydrogen or any of the following:

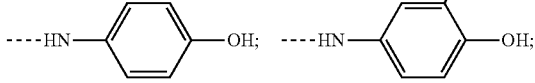

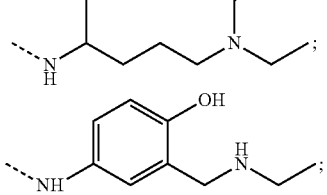

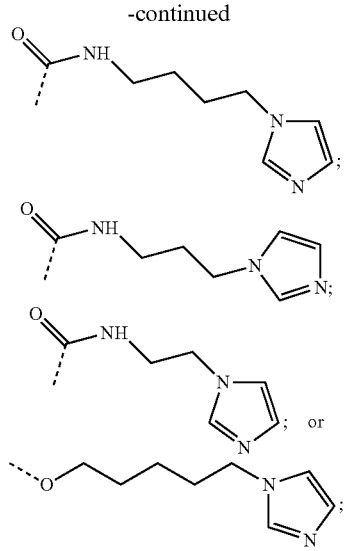

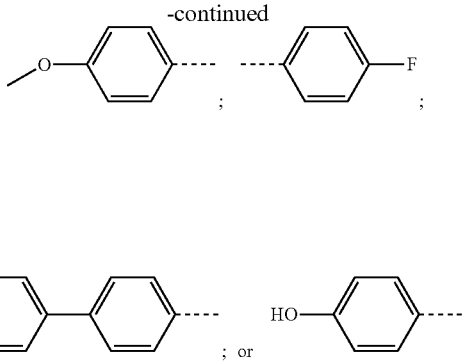

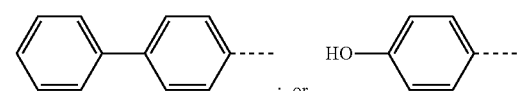

wherein the dashed line (- - - - -) represents a bond to Formula (III).

As another example, a compound described herein can be:

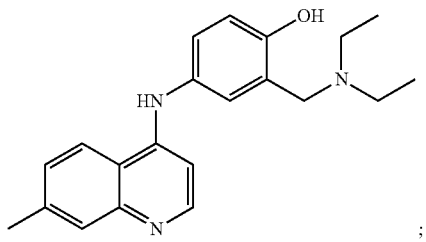

According to Formula (II), $R_4$ can represent hydrogen or a halogen (e.g., chloro).

According to Formula (II), $R_5$ can represent hydrogen or any of the following:

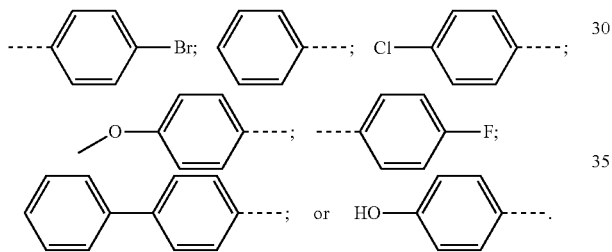

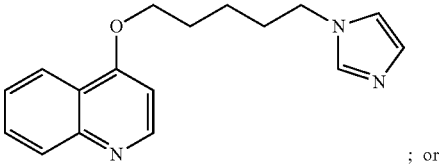

In the above structures, a dashed line (- - - - - -) represents a bond.

As another example, a compound described herein can be a compound of Formula (III):

Formula (III)

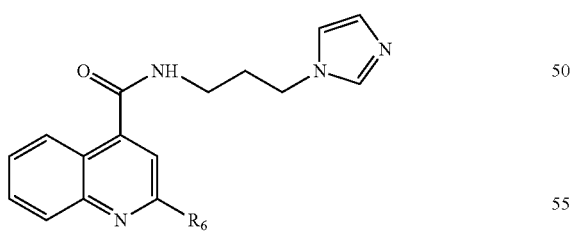

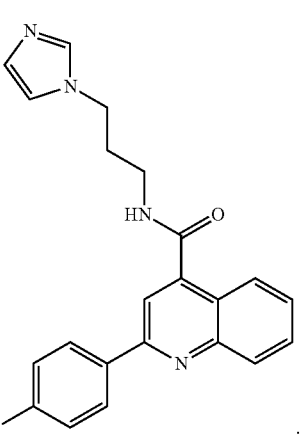

or a pharmaceutically acceptable salt, including all tautomers and stereoisomers thereof.

According to Formula (III), $R_6$ can represent hydrogen;

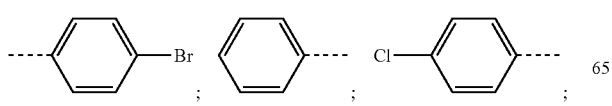

For example, a compound described herein can be compound SP138 having a structure as follows:

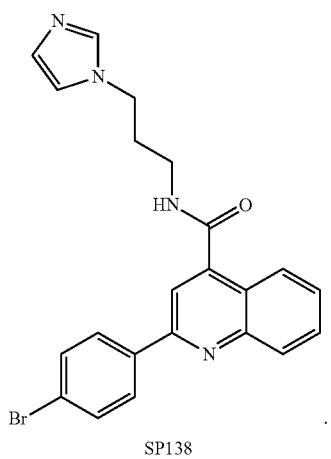 [SMILES: "SP138" ; O=C(NCCCn1ccnc1)c1cc(-c2ccc(Br)cc2)nc2ccccc12]

SP138

Acetylcholinesterase

Acetylcholinesterase (AChE), a carboxylesterase, is an efficient enzyme in the nervous system that has been implicated in proper synaptic transmission. AChE, also known as acetylhydrolase, is a serine protease that hydrolyzes the neurotransmitter acetylcholine.

AChE can be found at neuromuscular junctions and cholinergic brain synapses, where its activity serves to terminate synaptic transmission. In cholinergic brain synapses, AChE hydrolyzes the neurotransmitter acetylcholine (ACh) into acetic acid to rapidly terminate synaptic transmission and is responsible for transmitting impulses from one cell to another.

AChE inhibitors occur naturally in toxins and venoms but are also present in nerve gas and certain pesticides. Inhibiting AChE can result in an increase in ACh concentration throughout the nervous system, which can be deadly. A class of drugs known as AChE re-activators can be used to counteract the effect of these AChE inhibitors.

Enzyme Structure and Mechanism.

AChE has a very high catalytic activity. Each molecule of AChE degrades about 25,000 molecules of acetylcholine (ACh) per second, approaching the limit allowed by diffusion of the substrate. The active site of AChE comprises 2 subsites: the anionic site and the esteratic subsite. The structure and mechanism of action of AChE have been elucidated from the crystal structure of the enzyme.

The anionic subsite accommodates the positive quaternary amine of acetylcholine as well as other cationic substrates and inhibitors. The cationic substrates are not bound by a negatively-charged amino acid in the anionic site, but by interaction of 14 aromatic residues that line the gorge leading to the active site. All 14 amino acids in the aromatic gorge are highly conserved across different species. Among the aromatic amino acids, a substitution of alanine at tryptophan 84 results in a 3,000-fold decrease in reactivity. The gorge penetrates half way through the enzyme and is approximately 20 angstroms long. The active site is located 4 angstroms from the bottom of the molecule.

The esteratic subsite, where acetylcholine is hydrolyzed to acetate and choline, contains the catalytic triad of three amino acids: serine 200, histidine 440 and glutamate 327. These three amino acids are similar to the triad in other serine proteases except that the glutamate is the third member rather than asparate. Moreover, the triad is of opposite handedness to that of other proteases. The hydrolysis reaction of the carboxyl ester leads to the formation of an acyl-enzyme and free choline. Then, the acyl-enzyme undergoes nucleophilic attack by a water molecule, assisted by the histidine 440 group, liberating acetic acid and regenerating the free enzyme.

Biological Function.

During neurotransmission, ACh is released from the nerve into the synaptic cleft and binds to ACh receptors on the post-synaptic membrane, relaying the signal from the nerve. AChE, also located on the post-synaptic membrane, terminates the signal transmission by hydrolyzing ACh. The liberated choline is taken up again by the pre-synaptic nerve and ACh is synthesized by combining with acetyl-CoA through the action of choline acetyltransferase.

Disease Relevance.

For a cholinergic neuron to receive another impulse, ACh must be released from the ACh receptor. This occurs when the concentration of ACh in the synaptic cleft is very low. Inhibition of AChE leads to accumulation of ACh in the synaptic cleft and results in impeded neurotransmission.

Irreversible inhibitors of AChE may lead to muscular paralysis, convulsions, bronchial constriction, and death by asphyxiation. Organophosphates (OP), esters of phosphoric acid, are a class of irreversible AChE inhibitors. Cleavage of OP by AChE leaves a phosphoryl group in the esteratic site, which is slow to be hydrolyzed (on the order of days) and can become covalently bound. Irreversible AChE inhibitors have been used in insecticides (e.g., malathion) and nerve gases for chemical warfare (e.g., Sarin and Soman). Carbamates, esters of N-methyl carbamic acid, are AChE inhibitors that hydrolyze in hours and have been used for medical purposes (e.g., physostigmine for the treatment of glaucoma). Reversible inhibitors occupy the esteratic site for short periods of time (seconds to minutes) and can be used to treat of a range of central nervous system diseases. Tetrohydroaminoacridine (THA) and donepezil are FDA-approved to improve cognitive function in Alzheimer's disease. Rivastigmine is also used to treat Alzheimer's and Lewy body dementia, and pyridostigmine bromide is used to treat myasthenia gravis. Alzheimer disease drugs donepezil, galantamin, and rivstigmin are inhibitors of acetylcholinesterase as well.

A compound that reverses inactivation of acetylcholinesterase can be used for modulation of neuronal signaling and transmission.

An endogenous inhibitor of AChE in neurons is Mir-132 microRNA, which may limit inflammation in the brain by silencing the expression of this protein and allowing ACh to act in an anti-inflammatory capacity.

It has also been shown that the main active ingredient in cannabis, tetrahydrocannibinol, is a competitive inhibitor of acetylcholinesterase.

Distribution.

AChE is found in many types of conducting tissue: nerve and muscle, central and peripheral tissues, motor and sensory fibers, and cholinergic and noncholinergic fibers. The activity of AChE is higher in motor neurons than in sensory neurons.

Acetylcholinesterase is also found on the red blood cell membranes, where it constitutes the Yt blood group antigen. Acetylcholinesterase exists in multiple molecular forms, which possess similar catalytic properties, but differ in their oligomeric assembly and mode of attachment to the cell surface.

AChE Gene.

In mammals, acetylcholinesterase is encoded by a single AChE gene while some invertebrates have multiple acetylcholinesterase genes. Diversity in the transcribed products from the sole mammalian gene arises from alternative mRNA splicing and post-translational associations of catalytic and structural subunits. There are three known forms: T (tail), R (read through), and H (hydrophobic).

$AChE_T$

The major form of acetylcholinesterase found in brain, muscle, and other tissues, known as is the hydrophilic species, which forms disulfide-linked oligomers with collagenous, or lipid-containing structural subunits. In the neuromuscular junctions AChE expresses in asymmetric form which associates with ColQ or subunit. In the central nervous system it is associated with PRiMA which stands for Proline Rich Membrane anchor to form symmetric form. In either case, the ColQ or PRiMA anchor serves to maintain the enzyme in the intercellular junction, ColQ for the neuromuscular junction and PRiMA for synapses.

$AChE_H$

The other, alternatively-spliced form expressed primarily in the erythroid tissues, differs at the C-terminus, and contains a cleavable hydrophobic peptide with a PI-anchor site. It associates with membranes through the phosphoinositide (PI) moieties added post-translationally $AChE_R$ The third type has, so far, only been found in *Torpedo* sp. and mice although it is hypothesized in other species. It is thought to be involved in the stress response and, possibly, inflammation.

Molecular Engineering

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art. Generally, conservative substitutions can be made at any position so long as the required activity is retained.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6$ ($\log_{10}[Na^+]$)$+0.41$(fraction G/C content)$-0.63$ (% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (sRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several sRNA molecule design programs using a variety of algorithms are known to the art (see e.g., Cenix algorithm, Ambion; BLOCK-iT™ RNAi Designer, Invitrogen; sRNA Whitehead Institute Design Tools, Bioinformatics & Research Computing). Traits influential in defining optimal sRNA sequences include G/C content at the termini of the siRNAs, Tm of specific internal domains of the sRNA, sRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating nerve agent exposure or accidental organophosphate poisoning in a subject in need of administration of a therapeutically effective amount of a compound described herein, so as to reverse inactivation of AChE. Further discussion refers to AChE, but one of ordinary skill will understand that methods or compounds described herein can be used in conjunction with AChE variants, which retain AChE activity.

Compounds and methods provided herein describe the therapeutic potential to treat or reverse the symptoms of exposure to agents such as nerve agents or pesticides. Provided herein are methods for the use of analogs in prophylaxis of the exposure to agents such as nerve agents or pesticides. Also provided are methods for the ability to use compounds as described herein at low doses and the ability to cross the blood brain barrier due to a unique mechanism of action.

Further, methods for prophylactic and therapeutic uses of drugs (e.g., antimalarial) and their analogs are provided herein. Disclosed herein are methods for the selection of candidates for prophylactic or therapeutic applications. First, a comprehensive structure-activity relationship (SAR) through exhaustive characterization of medicinal chemistry space can be established around compound SP138, including but not limited to understanding the functionalities that lead to fast and broad (i.e., against multiple agents) reactivation while keeping candidates non-toxic and soluble. Second, non-toxic, orally available, and metabolically stable compounds that are able to reactivate AChE across the blood-brain barrier in the in vivo model can be identified.

The compounds as described herein have been demonstrated to be: (i) more efficient than 2-PAM by in vitro measures (i.e., have a faster rate of reactivation and at lower compound concentrations); (ii) not inhibitory to the enzyme itself at the concentrations needed to achieve considerable reactivation (high $K_i$); (iii) effective at restoring nearly full activity to DFP-inhibited AChE (whereas, 2-PAM achieves ~50% only at much higher concentrations); (iv) active against a sarin analog (NIMP); (v) hydrophobic and tolerant to modifications, i.e., likely to yield, upon optimization, compounds that are sufficiently soluble, cross blood-brain barrier, and are orally available; and (vi) able to decrease mortality in mice upon challenge with DFP at relatively low doses (an 100-fold molar excess of 2-PAM was shown to be needed in order to have similarly protective effects).

Organophosphate-based nerve agents remain a threat to military personnel, and one way to reduce this threat is to develop a class of compounds that can be broadly administered in anticipation of exposure that would minimize ensuing toxic effects. Compounds described herein can be useful for treatment or prophylaxis given their efficacy against a wide range of OP agents, non-toxicity even with prolonged use (e.g., during the full length of deployment), or oral availability (or deliverable via patch).

Nerve agents are understood as a class of phosphorus-containing organic chemicals (organophosphates) that can disrupt the mechanism by which nerves transfer messages to organs. The disruption can be caused by blocking acetylcholinesterase, an enzyme that normally relaxes the activity of acetylcholine, a neurotransmitter. A nerve agent can include a G-series (non-persistent) nerve agent, a V-series (persistent) nerve agent, or a Novichok nerve agent. A nerve agent can include GA (tabun), GB (sarin), GD (soman), cyclosarin (GF), VE, VG (amiton), VM, VR, VX, or a Tammelin ester.

Agents of organophosphate poisoning can include insecticides such as dichlorvos, malathion, or parathion. Agents of organophosphate poisoning can include phenothiazines.

Methods described herein are generally performed on a subject in need thereof. A subject in need of the therapeutic methods described herein can be a subject having, diagnosed with, suspected of having, or at risk for developing nerve agent exposure or accidental organophosphate poisoning. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, guinea pigs, and chickens, and humans. For example, the subject can be a human subject.

An effective amount of a compound described herein is generally that which can reverse inactivation of AChE in a subject.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of compound described herein can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reverse inactivation of AChE.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

Dosage experiments in BALB mice with ADOC at up to 120 mg/kg showed no effect on mice up to seven days after injection. Livers of mice treated with the maximum dose were harvested, sectioned and histology showed no pathomorphological changes. Based on structural similarity of ADOC to Tylenol, it is estimated that a non-toxic dose could go up to at least 200 mg/kg.

DFP challenge experiments at the dose that led to very efficient inhibition of AChE in tissues, and cumulative control experiments, which resulted in a total of 14/15 mice dying within an hour of administration (indicating that this was close to an LD90+). Mice were injected with a total of 120 mg/kg ADOC ip 20 minutes prior to and 5 minutes post-administration of DFP (this timing was used to achieve high concentration of ADOC in blood regardless of further pharmacokinetics). While the experiment was designed to study in vivo reactivation, not survival, all injected mice (5/5) survived for 24 hours after the challenge. Tissues, including compartments and blood, from mice treated with ADOC showed significant reactivation in comparison to non-treated controls (see e.g., FIG. 24C).

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Shamel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Administration of a compound described herein can occur as a single event or over a time course of treatment. For example, a compound described herein can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for nerve agent exposure or accidental organophosphate poisoning, or reversing inactivation of AChE.

A compound described herein can be administered simultaneously or sequentially with another agent, such as an antibiotic, an antiinflammatory, or another agent. For example, a compound described herein can be administered simultaneously with another agent, such as an antibiotic or an antiinflammatory. Simultaneous administration can occur through administration of separate compositions, each containing one or more of a compound described herein, an antibiotic, an antiinflammatory, or another agent. Simultaneous administration can occur through administration of one composition containing two or more of a compound described herein, an antibiotic, an antiinflammatory, or another agent. A compound described herein can be administered sequentially with an antibiotic, an antiinflammatory, or another agent. For example, a compound described herein can be administered before or after administration of an antibiotic, an antiinflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition is administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to compounds described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Systematic Exploration of the AChE and Small Molecule Interaction

The following example describes systematic experiments determining small molecule interaction with AChE and small molecule effects on inhibition, aging and reactivation of AChE (see e.g., FIG. 1). The objective of the study was to identified small molecules involved in the inhibition, aging and reactivation steps to be used for activators, protecting agents, allosteric reactivators, reactivating potentiators and new reactivators, broad reactivators, or anti-aging protecting agents.

Example 2: Acetylcholinesterase (AChE) Assay

Figure 2:
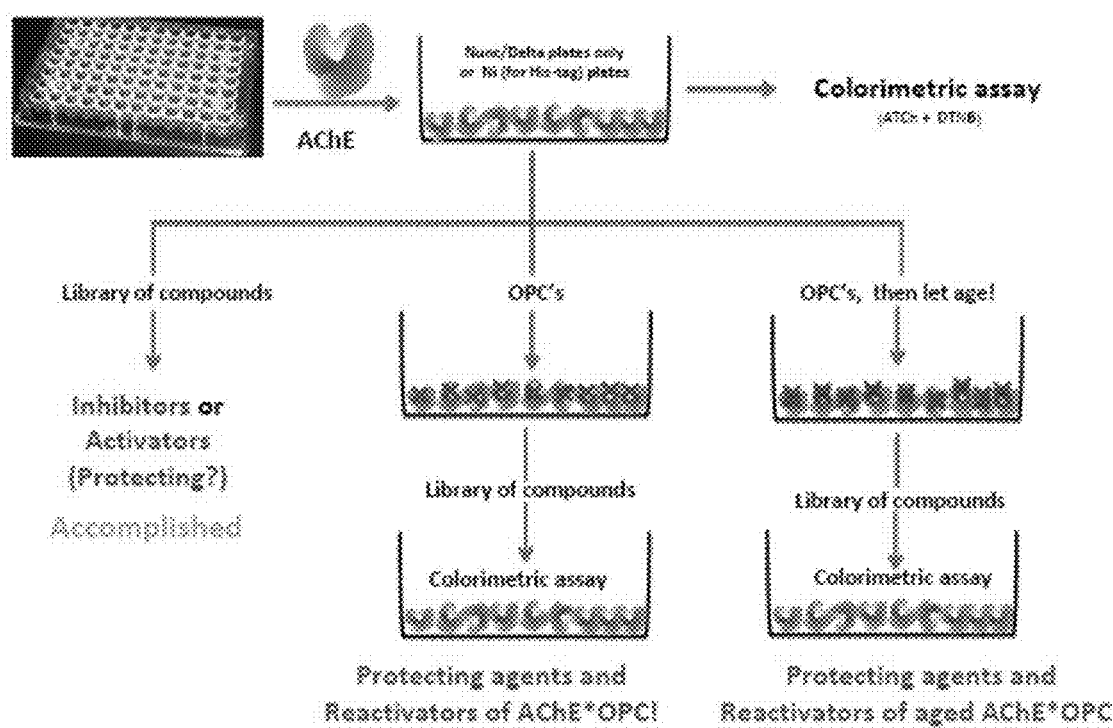
FIG. 2 is an illustration of the assays used for the screening of inhibitors, activators or protectors. This diagram depicts the experiments performed to identify and characterize small molecules for use as inhibitors or activators. Further details can be found in Example 2.

The following example describes the AChE assay platforms (see e.g., FIG. 2). This example also describes a novel method to assay AChE activity following attachment of the enzymes to a solid support (e.g., a 96-well plate), allowing for the ability to modify the AChE, wash away excess modifier and test the effect of the modifier on AChE activity.

The novel assay method immobilizes AChE and is gentle enough to allow the enzyme to stay intact and retain full activity.

As illustrated in FIG. 2, four types of experiments were performed.

A 96-well plate was loaded with AChE and
(1) a colorimetric assay was performed;
(2) a library of compounds consisting of inhibitors, activators or protectors were screened;
(3) organic phosphorous compounds were introduced to the AChE to form a complex:
  (a) a library of compounds were screened, then a colorimetric assay was performed; or
  (b) the complex was allowed to age before the library of compounds were screened, then a colorimetric assay was performed.

The solid state assay was shown to be used for high-throughput screening for reactivators of AChE. The solid state assay can be used for the detection and measurement of AChE activity in the presence of agents. Examples of agents that can be detected include nerve agents and pesticides.

This example further describes the characterization of the solid-phase assay technique, determining the stability of the enzyme in the solid-phase, a variety of plating conditions and the versatility of the technique used with other enzymes. This example further provides for a method to provide a rapid, inexpensive way to test multiple samples for AChE activity.

Example 3: Screening of AChE Activators/Reactivators

The following example describes the screening of compounds that activate AChE activity after a solid-phase activity assay was performed. The objective of this study was to identify activators of AChE.

This example demonstrates the immobilization of the AChE on a 96-well plate, excess AChE was washed away, an excess of inhibitor (e.g., sof DIPF or paraoxon) was added to inhibit AChE, inhibitory agents were washed away, then incubated with a 10 µM concentration of the compound being screened (e.g., from the Spectrum Collection library) for reactivation activity. Reactivation activity of the screened compound was measured.

Figures 3A, 3B, 3C, 3D, 3E, 3F, 3G, 3H, 3I, 3J:
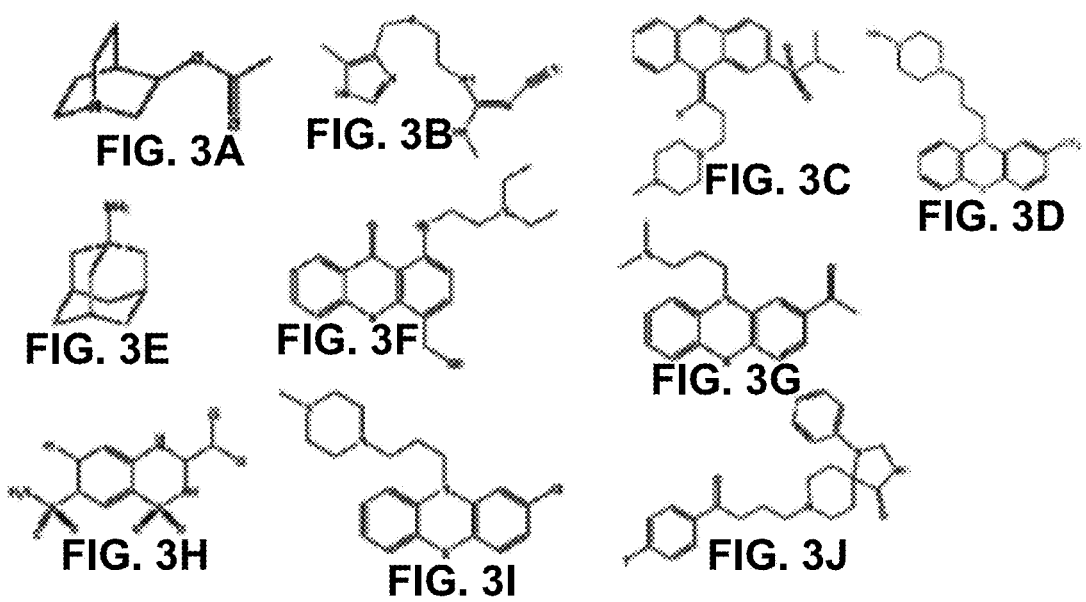
FIG. 3A-3J shows molecular structures of identified AChE activators. Further details regarding the identification of these molecules can be found in Example 3.

The screening procedure identified 77 inhibitors and 10 significant activators (at 10 µM) (see e.g., FIG. 3). A large number of significant activators were identified at a concentration of at least 100 µM.

Amodiaquine was determined to be a reactivator at far lower concentrations than standard reactivators ($K_a$~3 µM). Because the concentration for the compound to provide reactivation is low, the reactivation can be achieved in vivo. Scopoletin was also determined to have reactivation activity that is comparable to pralidoxine activity.

This example further provides for the testing of expansion libraries to determine the structure-activity relationship (SAR). Compounds such as 2-(4,5-Dihydro-1H-imidizol-2-yl)phenol, 97%; 6-(Morpholin-4-yl-(3,4,5-trimethoxy-phenyl)-methyl)-benzo(1,3)dioxol-5-ol; 2-(4-Bromo-phenox)-3-(3-dimethylaminomethyl-2,4-dihydroxy-phenyl)-ethanone; 1-Piperidinomethyl-2-napthol; 8-((Dimethylamino)me)-3-(2-fluorophenoxy)-7-hydroxy-2-methyl-4H-chromoen-4-one; and 1-Morpholinomethyl-2-napthol were identified as reactivators. Further compounds identified as reactivators include 2-[(dimethylamino) methyl]-4-(1,1,3,3-tetramethylbutyl)phenol; 2,4-Bis[(dimethylamino)methyl]-6-methylphenol; and 7-Chloro-4-(4-hydroxyanilino)quinoline.

This study showed the structure-activity relationship and mechanism of stimulation of a family of compounds.

Example 4: Screening of AChE Inhibitors

The following example describes an experiment identifying inhibitors which protect AChE from irreversible AChE inhibitors (e.g., diisopropyl fluorophosphate (DFP)). The objective of this study is to identify and characterize inhibitors of AChE that also protect.

This example shows the assay determined that inhibitor, donepezil, protects AChE from diisopropyl fluorophosphate (DFP), at nM concentrations (see e.g., FIG. 4). It is envisioned that donepezil will be a safer alternative to pyridostigmine.

Example 5: Characterization of AChE Allosteric Activators

The following example characterizes allosteric activators identified from screening assay. The objective of this study was to identify and characterize allosteric activators of AChE.

Identified activators include amantadine, memantine, rimantadine, lysine, and arginine. This example shows the activity of AChE (see e.g., FIG. 5). Activity of AChE was enhanced when an activator was added. This example further describes dose-dependent protection. Amantadine was shown to provide protection at both 50 and 500 μM. Amantadine provided enhanced protection at 500 μM (see e.g., FIG. 5).

Figure 6A:
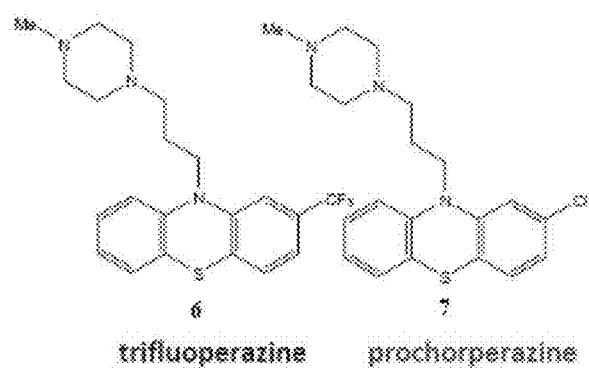
FIG. 6A is a series of chemical structures, trifluoperazine and prochlorperazine. Further details can be found in Example 5.
Figure 6B:
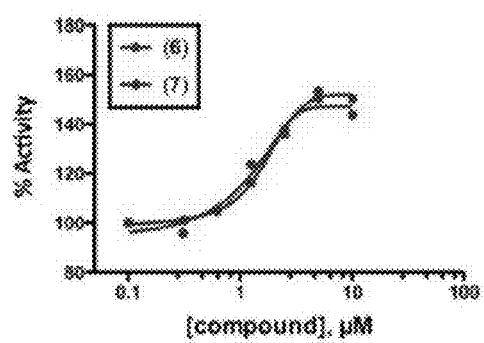
FIG. 6B is an activation curve demonstrating structure-activity relationship of activating compounds. Further details can be found in Example 5.
Figure 6C:
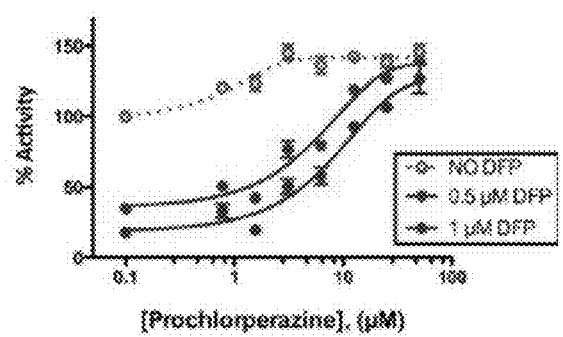
FIG. 6C is a protection curve. Further details can be found in Example 5.

Additional identified activators that also protect against DFP include trifluoperazine and prochlorperazine. Trifluoperazine and prochlorperazine possess similar AChE activity profiles (see e.g., FIG. 6). Enzyme protection was tested with various concentrations of compound prochlorperazine and DFP. Prochlorperazine was shown to be an effective protector at various concentrations of prochlorperazine and DFP (see e.g., FIG. 6).

Activity profiles were generated for compounds: prochlorperazine, chlorperazine, acepromazine, imipramine, desimpramine, amitriptyline, doxepin and custom-synthesized 5-[3-(4-Methyl-piperazine-1-yl)-propyl]-10,11-dihydro-5H-dibenzo[b,f]azepeine (see e.g., FIG. 7). Activity was shown to decrease for the custom made compound (see e.g., FIG. 7) when compared to prochlorperazine (7).

Example 6: Characterization of AChE Reactivators

Further examples of reactivators of AChE are amodiaquine, cloxacillin and scopoletin (see e.g., FIG. 8). The objective of this study was to identify and characterize reactivators of AChE.

A dose-dependent reactivation profile of DiPF-inhibited AChE was generated with various concentrations of compounds amodiaquine, chloroquine, desethyl-amodiaquine and pralidoxine (control) (see e.g., FIG. 9) to compare dose-dependent activities of the compounds.

Figure 10A:
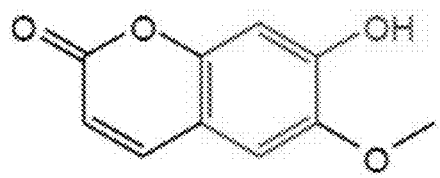
FIG. 10A-10C is a series of chemical structures and respective dose-dependent activity profiles. The activity profile shows the reactivation of paraoxon-inhibited AChE. The activity profile shows structure activity relationship when compared to other compounds. Further details can be found in Example 6.
Figure 10B:
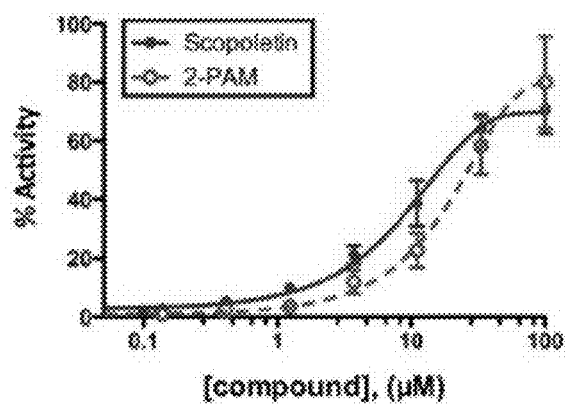
Figure 10C:

A dose-dependent reactivation profile of paraoxon-inhibited AChE was generated to determine the activity of scopoletin compared to pralidoxine (control) (see e.g., FIG. 10).

Figure 11A:
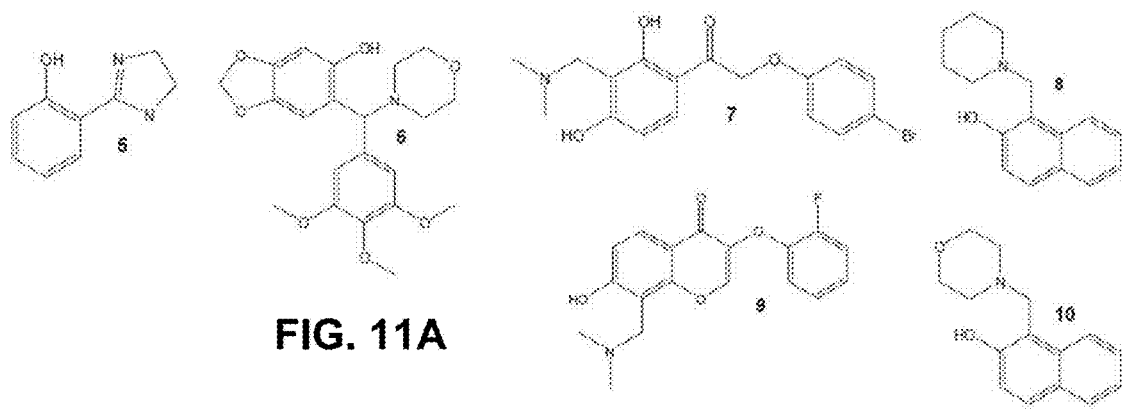
FIG. 11A-11B is a series of chemical structures of activators and their associated activity profiles at different concentrations. Further details can be found in Example 6.
Figure 11B:
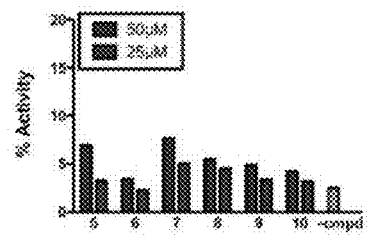

The example further describes the structure activity relationship (SAR) of small molecules inspired by scopoletin. Activity profiles of compounds 5-10 were measured at 25 μM and 50 μM concentrations (see e.g., FIG. 11).

Example 7: Design and Synthesis of AChE Reactivators

This example shows the design and synthesis of new derivatives of compounds designed to be a more efficient reactivator. It is envisioned that acidic, yet nucleophilic phenol(ate) can act as a nucleophile.

Figure 13A:
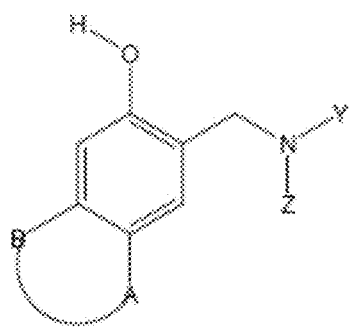
FIG. 13A-13C are a series of chemical structures of nucleophilic phenol compounds that reactivate AChE. Further details can be found in Example 7.
Figure 13B:
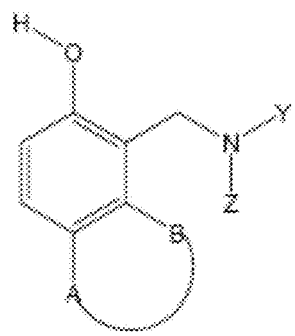
Figure 13C:
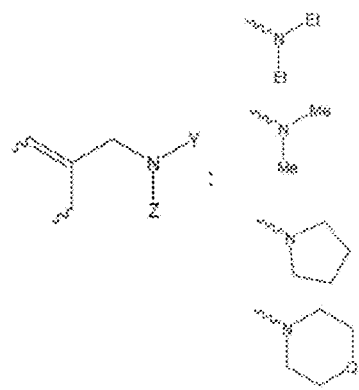
Figure 14A:
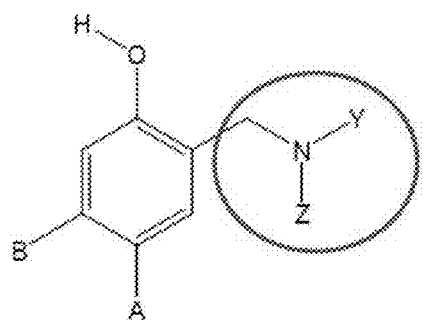
FIG. 14A-14B are a series of chemical structures of nucleophilic phenol compounds that reactivate AChE. Further details can be found in Example 7.
Figure 14B:
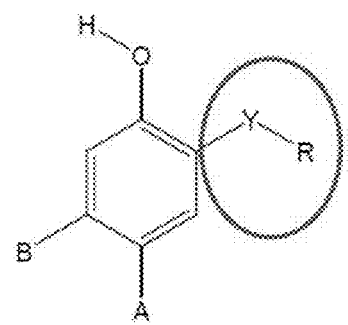
Figure 15A:
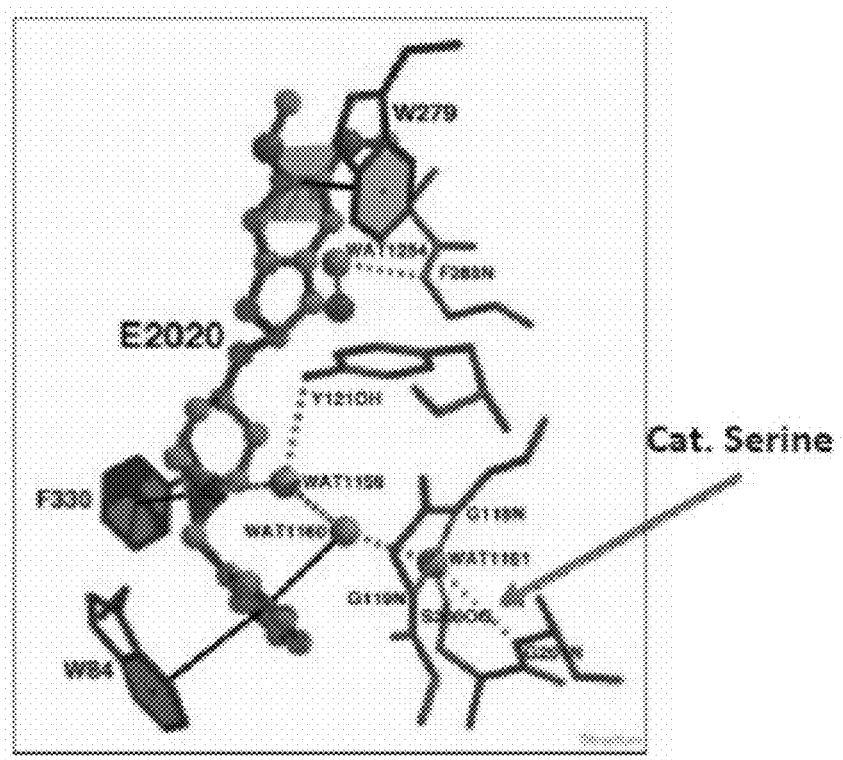
FIG. 15A is a depiction of the mechanism for reactivation of AChE.
Figure 15B:
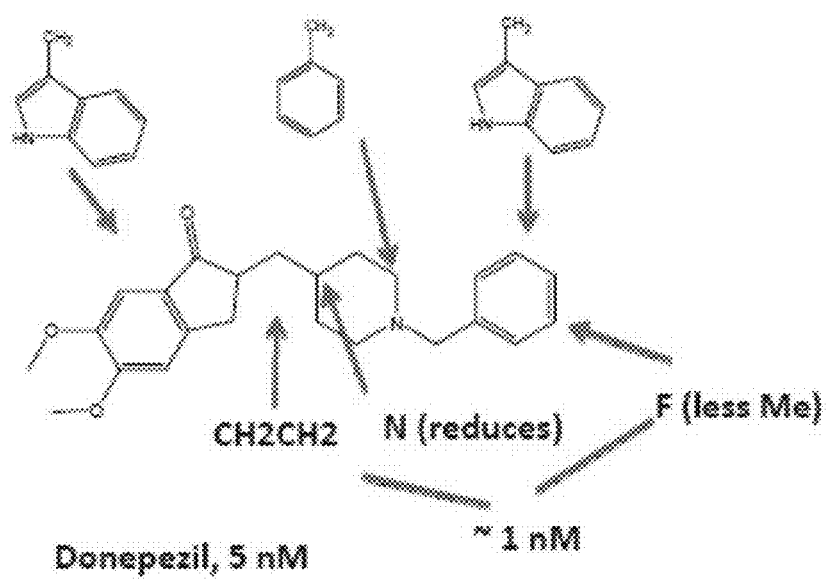
FIG. 15B is a depiction of the chemical reaction for reactivation of AChE.

This example provides for nucleophilic phenol compounds that reactivate AChE (see e.g., FIG. 12, FIG. 13, FIG. 14).

Example 8: Development of Imidazole-Based Reactivators of AChE

The following example describes the development of imidazole-based AChE reactivators. This example identified a class of imidazole-containing compounds that are effective both at preventing the inhibition of acetylcholinesterase (AChE) by organophosphates (OP) and at recovering activity of recently inhibited AChE.

The following example further demonstrates that the lead compound (SP138), chosen for its efficiency in reactivation of both paraoxon- and DFP-inhibited AChE, decreased mortality in mice challenged with DFP at doses at which 30-fold higher concentrations of 2-PAM were ineffective.

It was discovered that the antimalarial drug, amodiaquine, reactivates OP-inhibited AChE, a previously unreported activity. This example determined the mechanism of reactivation through SAR and co-crystallization in order to optimize reactivation. The in vivo efficacy was determined in a suitable animal model.

Analogs of amodiaquine were synthesized and tested in vitro for reactivation of AChE using a standard Ellman's assay. Compounds that efficiently reactivate AChE in vitro are then administered to live animals challenged with OP. Tissues from the animals are tested for reversal of OP-inhibition. Top candidates are being co-crystallized with AChE in order determine mechanistic details.

Example 9: Structure Activity Relationship (SAR) of Imidazole/Quinoline Compounds The following example describes the structure-activity relationship of imidazole/quinoline compounds compared to 2-PAM.

Figure 16:
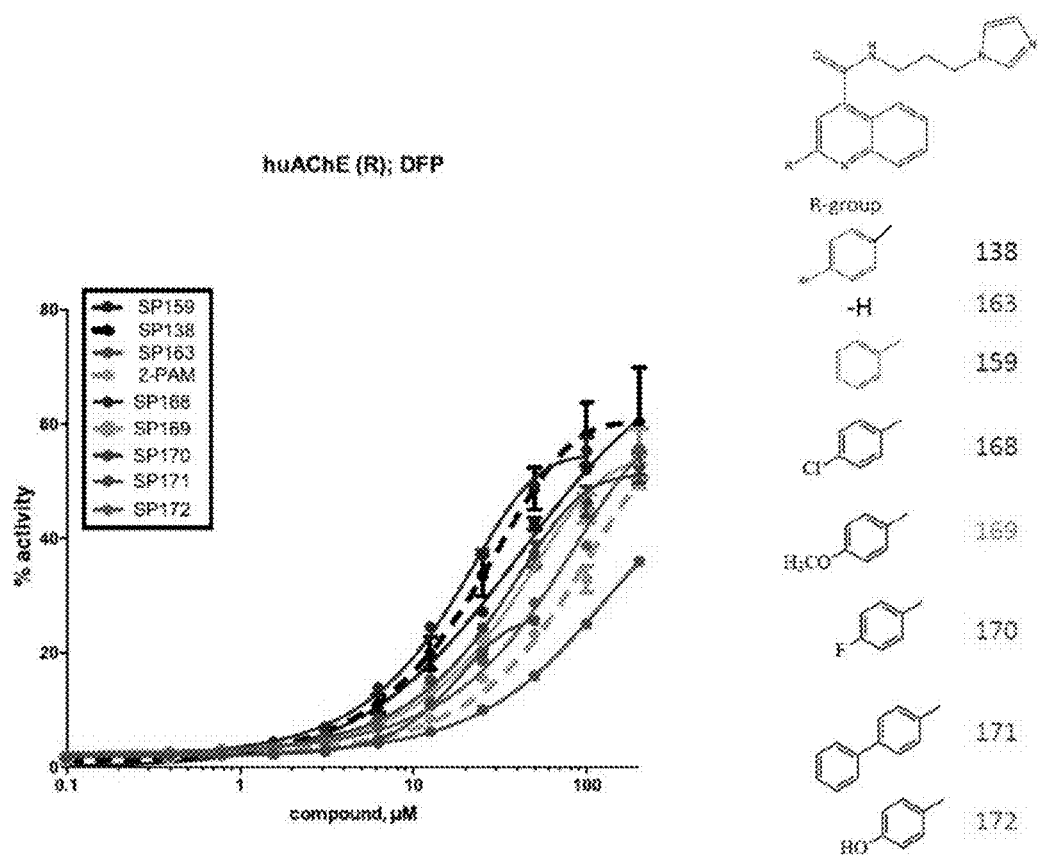
FIG. 16 is a dose-dependent activity profile of various compounds compared to PAM-2. Further details can be found in Example 9.

This example shows that a primary structure can be modified by R groups to modulate activity (see e.g., FIG. 16).

Example 10: Systematic Studies of Compound SP138 Imidazole/Quinoline Structure

Figure 17A:
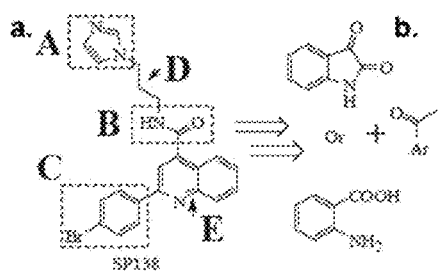
FIG. 17A-17C is a series of chemical structures and graphs. Further details can be found in Example 10.
Figure 17B:
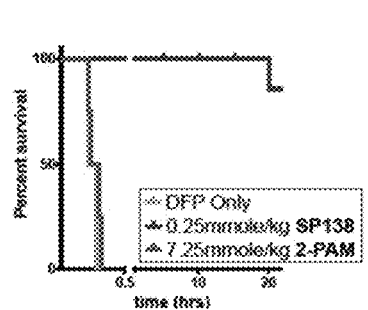
Figure 17C:
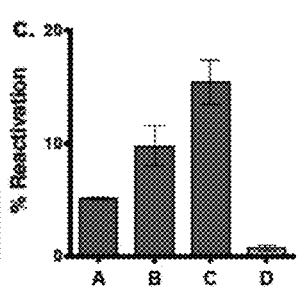

The following example describes the study of 5 domains of a lead molecule, survival analysis, and AChE activation. Examples of domains for study are shown in FIG. 17A. Survival analysis was performed with a lead molecule, SP138, compared with 2-PAM (see e.g., FIG. 17B). SP138 provided protection against DFP toxicity at concentrations at which 2-PAM was ineffective. Percent reactivation of AChE activity was determined in the brain treated with SP138 before and/or after DFP challenge (see e.g., FIG. 17C).

SP138 was demonstrated to prevent mortality in a mouse model and was not obviously toxic (showed no LD50 at 500 mg/kg—173 times the therapeutic dose—and induced no obvious distress in mice.

Example 11: Reactivation of DFP-Inhibited muAChE

Figure 18A:
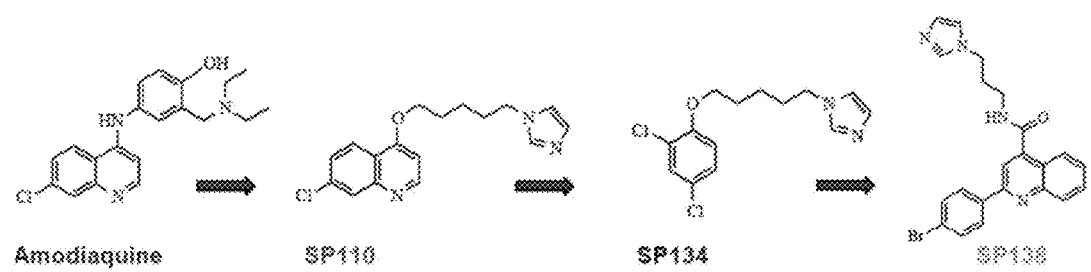
FIG. 18A is a series of chemical structures. Further details can be found in Example 11.
Figure 18B:
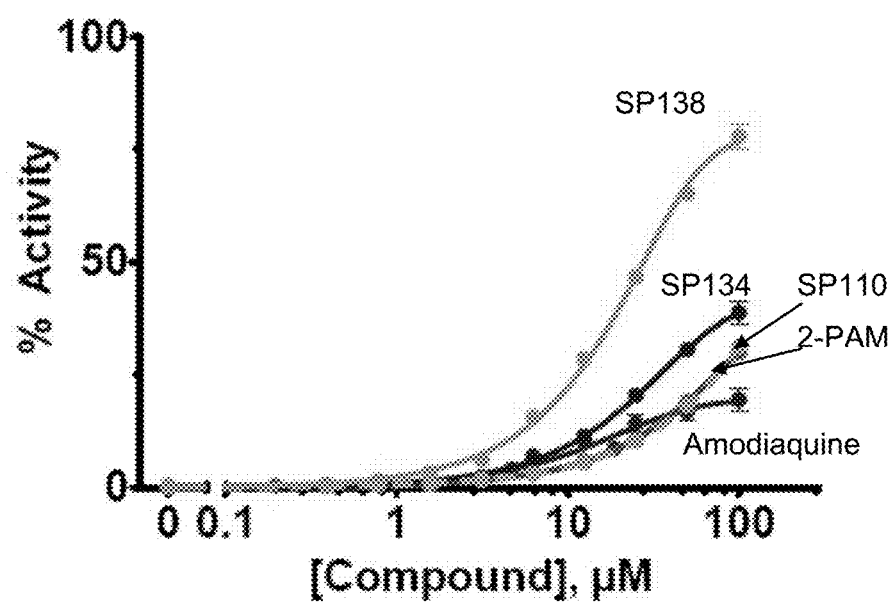
FIG. 18B is a line and scatter plot showing the reactivation of DFP inhibited muAChE. 2-PAM activity is shown in dashed gray. Further details can be found in Example 11.

The following example describes the activity of several quinoline- or imidazole-based compounds compared to 2-PAM. Compounds (see e.g., FIG. 18A) were added at the indicated concentrations and incubated 3 hours followed by dilution and addition of substrate. Activity was expressed in terms of full activity in the absence of inhibitor (see e.g., FIG. 18B). Results showed that compound SP138 had significantly greater activity than control (2-PAM). Compound SP134 also showed increased activity over control (2-PAM).

Example 12: Reactivation of Paraxon-Inhibited Brain Tissue

The following example describes the ex-vivo reactivation of reactivation of paraoxon-inhibited guinea pig brain tissue. Compounds (Amodiaquine, SP134, SP138, and 2-PAM) were added to brain tissue extracts from guinea pig challenged with paraoxon and then sacrificed (see e.g., FIG. 19A). Activity was expressed relative to activity seen in tissue from a control animal that had not been treated with paraoxon (see e.g., FIG. 19B).

Example 13: Compounds that Reactivate AChE

The following example describes the characterization of chemical compounds that reactivate AChE.

Figure 20A:
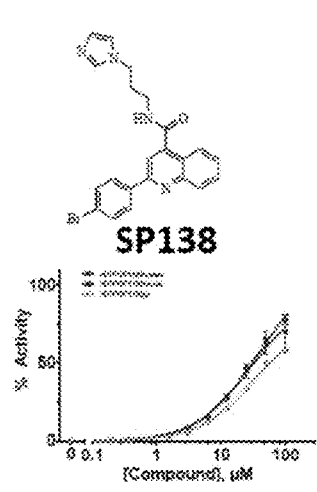
FIG. 20A is a chemical structure of SP138 and corresponding activity profile. Further details can be found in Example 13.
Figure 20B:
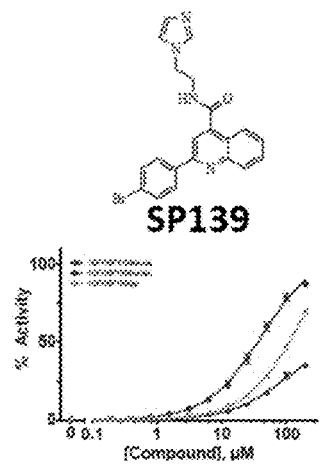
FIG. 20B is a chemical structure of SP139 and corresponding activity profile. Further details can be found in Example 13.
Figure 20C:
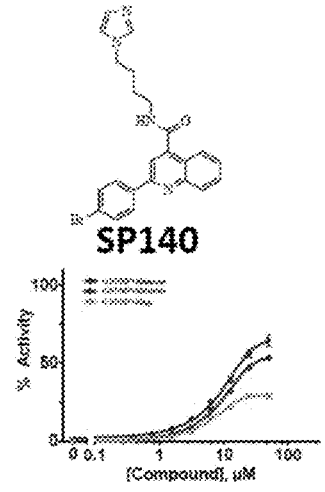
FIG. 20C is a chemical structure of SP140 and corresponding activity profile. Further details can be found in Example 13.

This example shows that the linker length can be tailored in imidazole/quinoline compounds to modulate activity (see e.g., FIG. 20). It was shown that one shorter or one longer linker provided favorable results, where two shorter or two longer was not as favorable.

Further, this example shows modification of R groups on imidazole/quinoline compounds can also modulate activity. The removal of bromine showed favorable results but the removal of the entire group was not as favorable (see e.g., FIG. 21).

This example also shows further activity studies with respect to linker length in imidazole compounds. It was shown that one shorter or one longer show favorable results, whereas two shorter or longer were not as favorable (see e.g., FIG. 22).

Example 14: Reactivation Functionality of ADOC

ADOC, the Mannich-base portion of amodiaquine (ADQ), was tested.

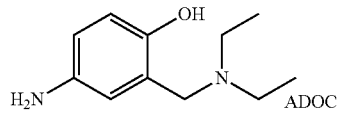

Figure 23A:
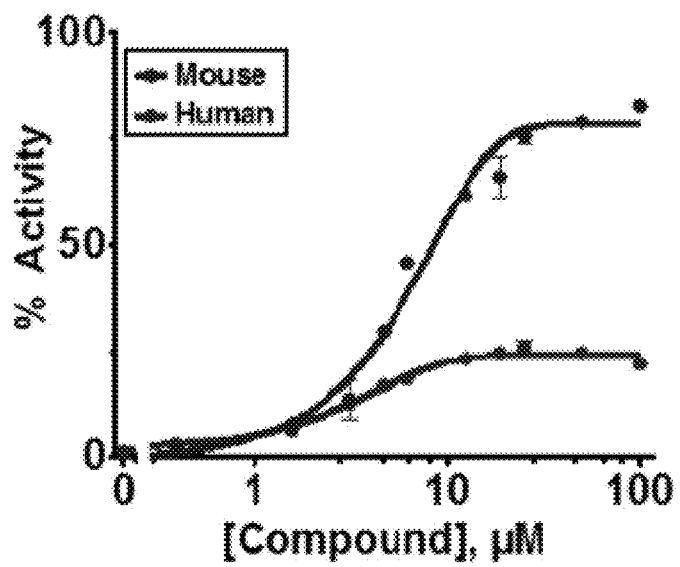
FIG. 23A-23D are a series of line and scatter plots showing reactivation of huAChE.
Figure 23B:
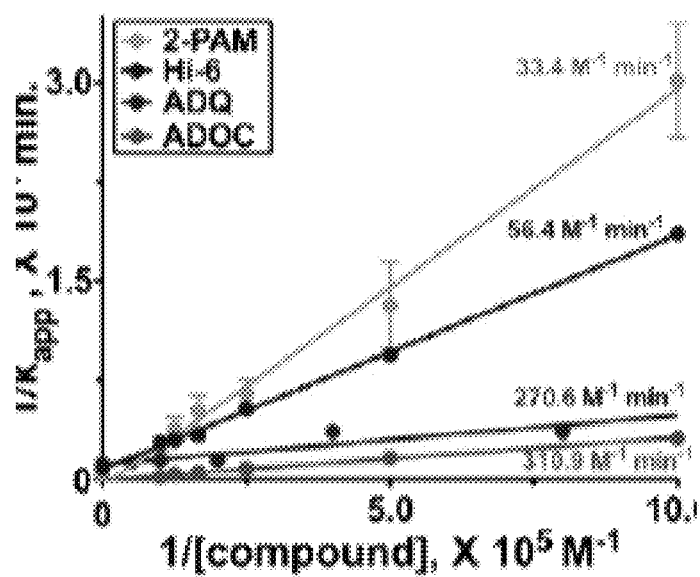
Figure 23C:
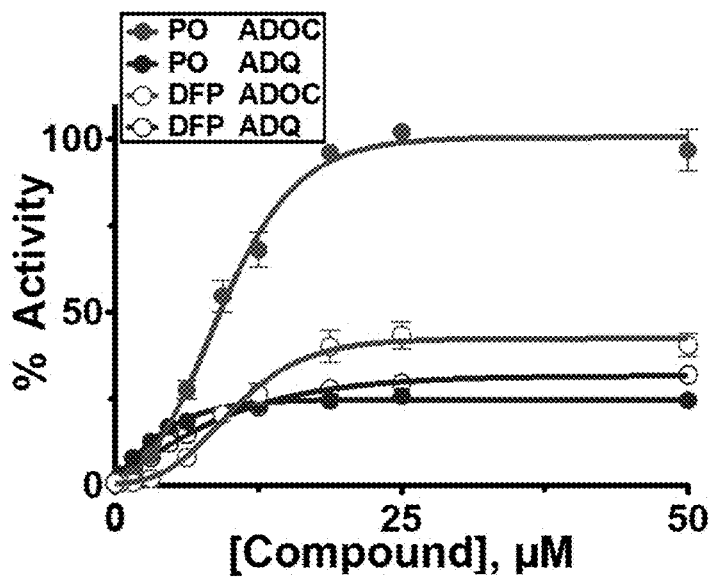

Results showed excellent reactivation of human AChE inhibited by paraoxon ($k_{r2}$ in FIG. 23B shows similar rates for ADQ and ADOC) and DFP-(FIG. 25A) at low concentrations. The dose-response for ADOC reactivation (FIG. 23C) was indicative of allosteric regulation and consistent with a second molecule binding to increase activity (the active site gorge of AChE has multiple hydrophobic/anionic binding sites). At concentrations at and above 40 μM, ADOC has higher effective rate (% activity at a given time point) than other compounds (including oximes), indicating strong potential for further optimization through anchoring; ADQ can be viewed as ADOC anchored to AChE gorge by a chloroquinoline group.

ADOC was also found to reactivate both sarin and VX inhibited forms of human AChE (results not shown).

Figure 23D:
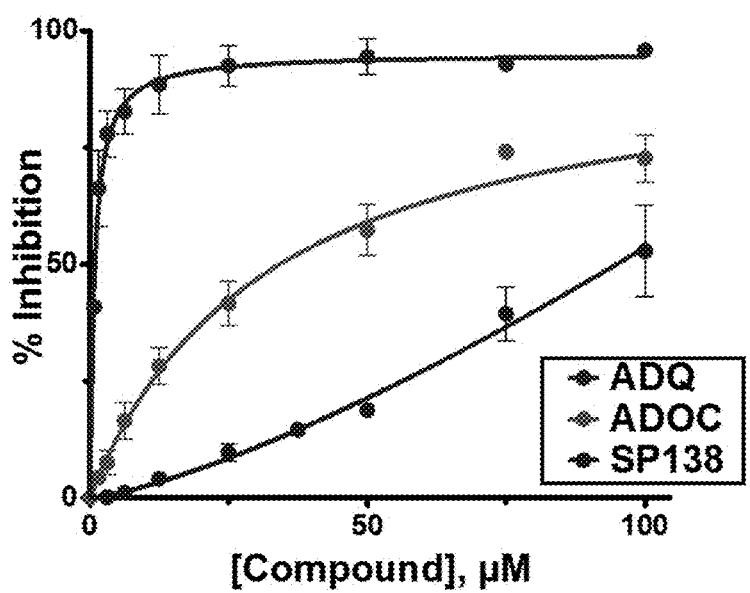

Experiments showed that SP138 is less inhibitory to AChE than ADQ or ADOC (see e.g., FIG. 23D). It is noted that such inhibition is reversible and significant reactivation of organophosphate-inactivation of AChE occurs below inhibitory concentrations of ADQ, ADOC, or SP138.

SIMP was tested for reactivation of AChE inhibited by SIMP, yielding a "soman-like" adduct (mixture of all diasteromers), poorly re-activatable by 2-PAM after aging (dealkylation) and obtained maximal activities comparable to HI-6 (see e.g., FIG. 24A), but requiring higher concentrations (due to stereo-chemical preferences of inhibition, aging, and reactivation, these results cannot be unambiguously attributed to the reversal of aging).

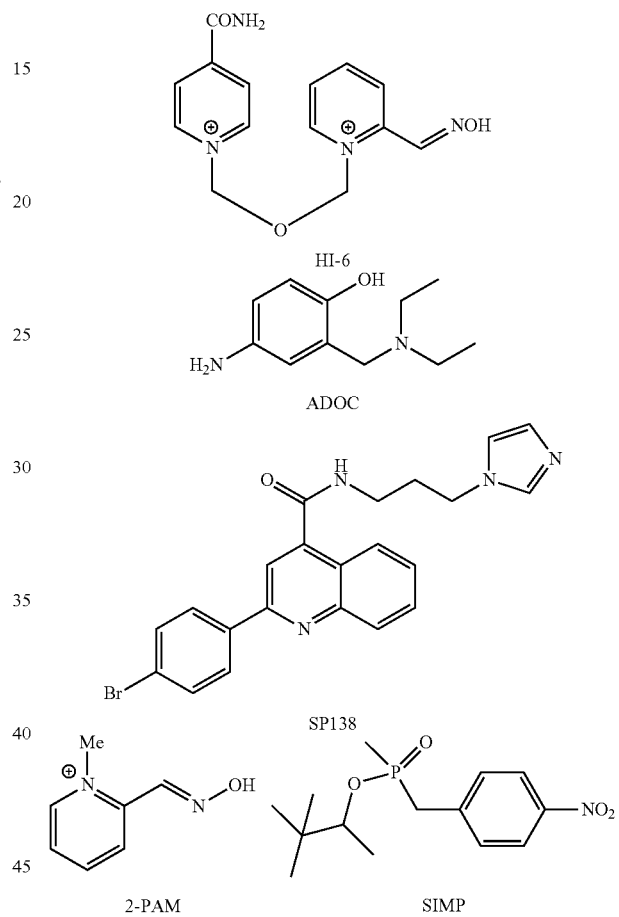

Example 15: Prophylaxis Model

The following example shows compounds of the present disclosure used for prophylactic protection from exposure to organophosphates.

Figure 26A:
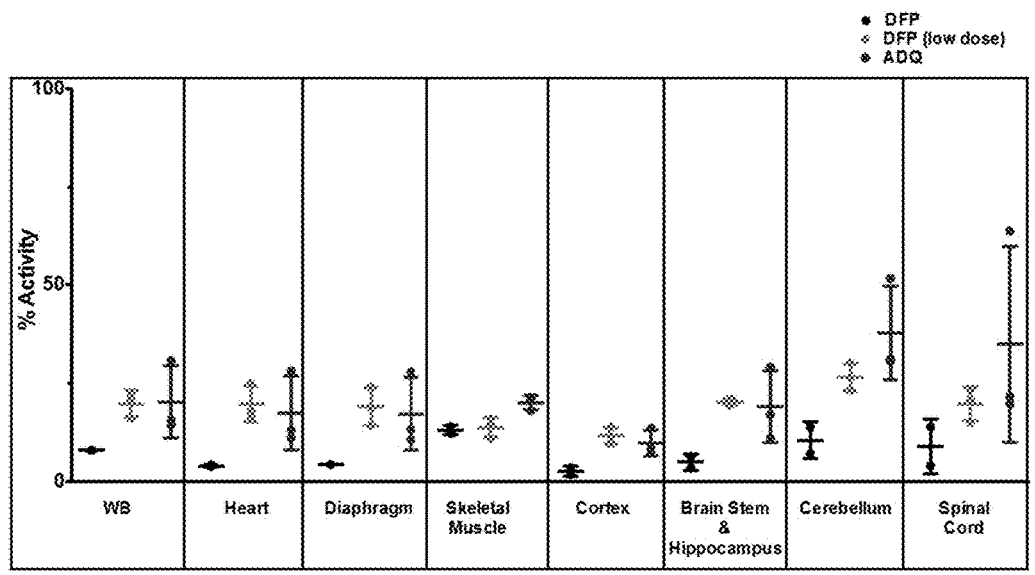
FIG. 26A-26C are a box plots showing tissue activity of AChE in surviving mice pre-treated with a prophylactic compound and treated with DFP.

ADQ (5 mg) was added to mouse feed 1 day prior to administration of 1.6×LD50 of s.c. DFP. In control mice (DFP only, no ADQ pre-treatment), seizures began in about 10 minutes and all control mice died within one hour. 3 out of 3 ADQ pre-treated mice survived 24 hours, at which time they were sacrificed, tissue was harvested, and AChE activity tested. Results showed that ADQ provides protection when given prophylactically, but tissue activity is relatively low (see e.g., FIG. 26A).

Figure 26B:
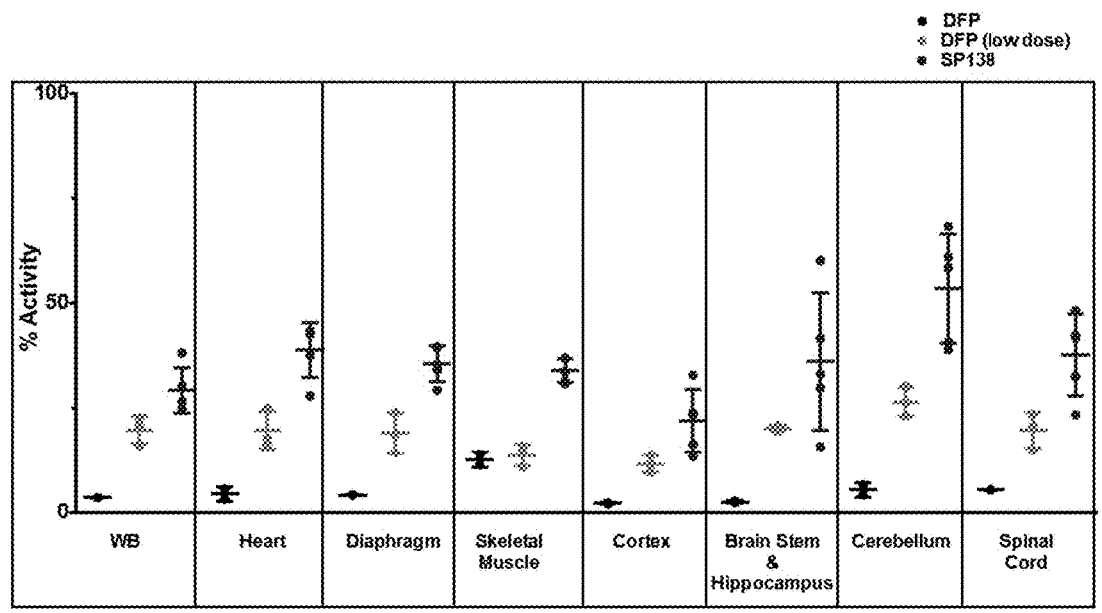

SP138 (5 mg) was added to mouse feed 1 day prior to administration of 1.6×LD50 of s.c. DFP. In control mice (DFP only, no SP138 pre-treatment), seizures began in about 10 minutes and 4 of 5 control mice died within about two hours. 5 out of 5 ADQ pre-treated mice survived 24 hours, at which time they were sacrificed, tissue was harvested, and AChE activity tested. Results showed that SP138 provides protection when given prophylactically, with better tissue activity compared to ADQ (see e.g., FIG. 26B).

Figure 26C:
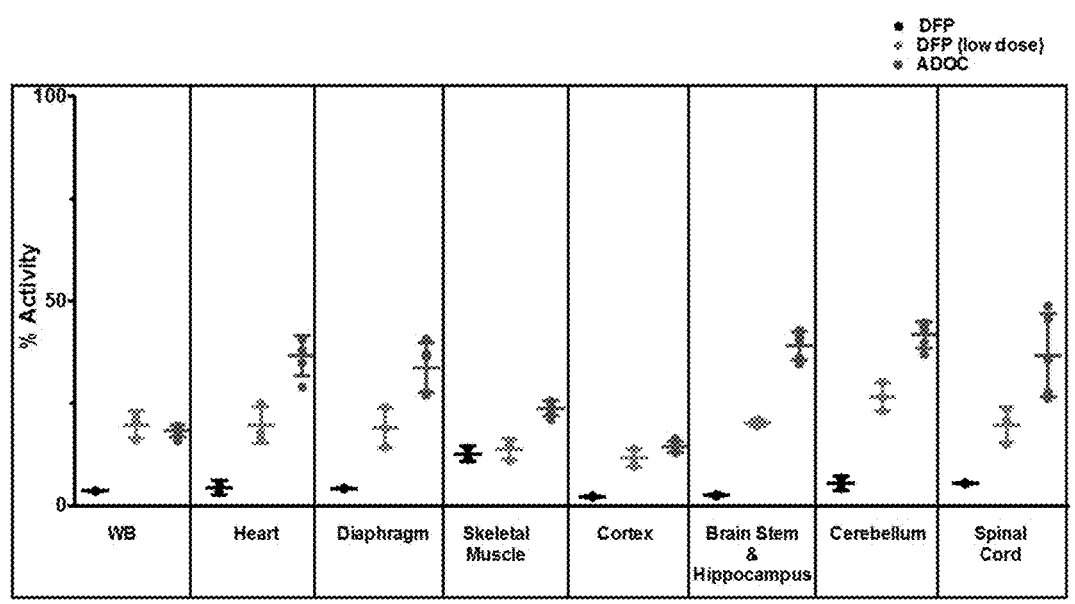

ADOC was administered to mice about 1-5 minutes after administration of 1.6×LD50 of s.c. DFP. In control mice (DFP only, no ADOC treatment), seizures began in about 10 minutes and all control mice died in less than one hour. 5 out of 5 ADOC treated mice survived 24 hours, at which time they were sacrificed, tissue was harvested, and AChE activity tested. Results showed that ADOC prevents mortality after a lethal dose of DFP (see e.g., FIG. 26C). Solubility of ADOC allows post-exposure protection.

As shown above, SP138 fed to mice one day prior to exposure to organophosphate offers complete protection from lethality. Also, ADOC given one dose prior and one dose post exposure provides complete protection (results not shown). It was shown that ADOC given just post-exposure provided complete protection. Tissue analysis, from animals treated with ADOC or SP138 and challenged with lethal levels of DFP, showed levels of AChE activity that were higher than animals treated with a very low dose of DFP. ADOC was very active at reactivating AChE inhibited by real nerve agents: VX, VR, GA, GB, and GF (results not shown).

In vitro, it was shown that human BuChE is also reactivated by amodiaquine and amodiaquine-like compounds (e.g., SP134), indicating an additional use for these compounds as a cofactor to a traditional bioscavenger treatment approach.

Example 16: Toxicity of ADOC

The following example shows toxicity studies for ADOC.

Figure 27A:
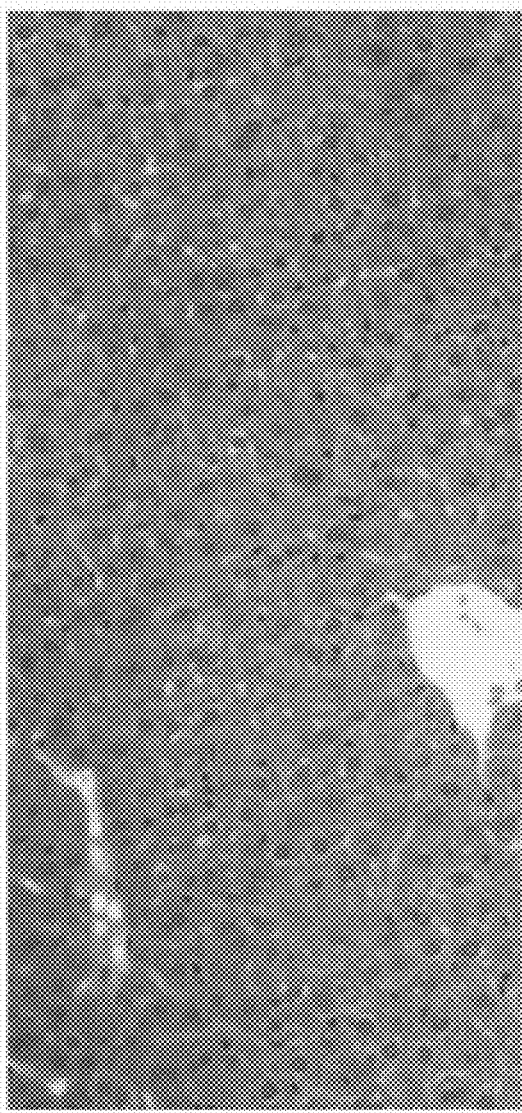
FIG. 27A-27B are a pair of images showing liver histology of mice.
Figure 27B:
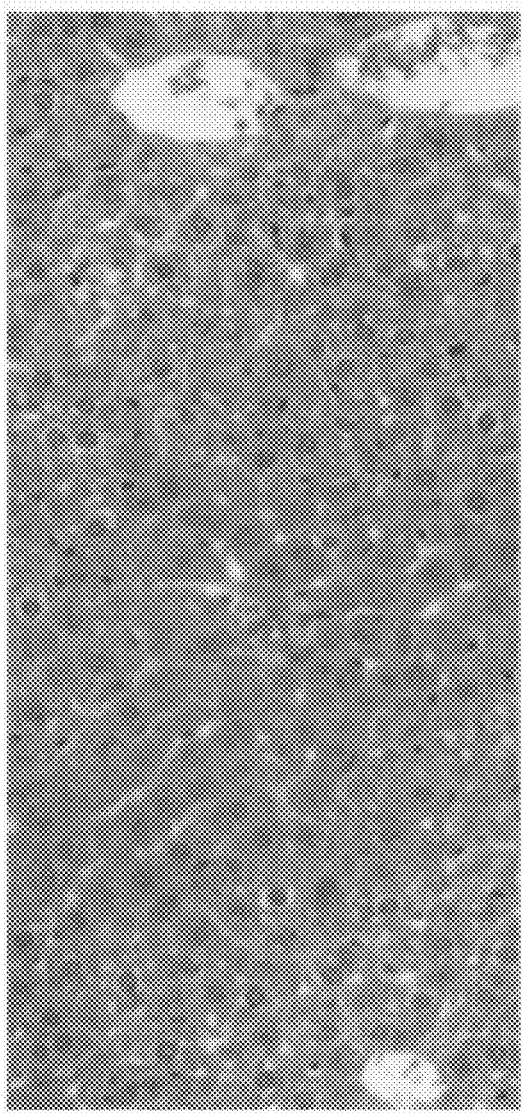

BALB mice were administered ADOC at up to 120 mg/kg by injection. Results showed no effect on mice up to seven days after injection. Livers of mice treated with the maximum dose were harvested, sectioned and histology showed no pathomorphological changes (see e.g., FIG. 27).

Based on structural similarity of ADOC to Tylenol, it is estimated that a non-toxic dose could go up to at least 200 mg/kg.

Example 17: Reactivation of BuChE

The following example shows reactivation of human BuChE by amodiaquine and analogs thereof.

Compounds amodiaquine, #17, SP110, SP134, and 2-PAM were tested for reactivation of BuChE that was inactivated by Paraoxon.

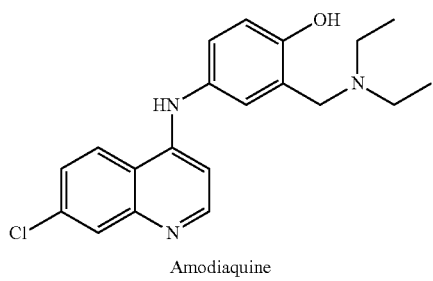

Amodiaquine

-continued

17

SP110

SP134

SP138

Perchlorperazine

Figure 28A:
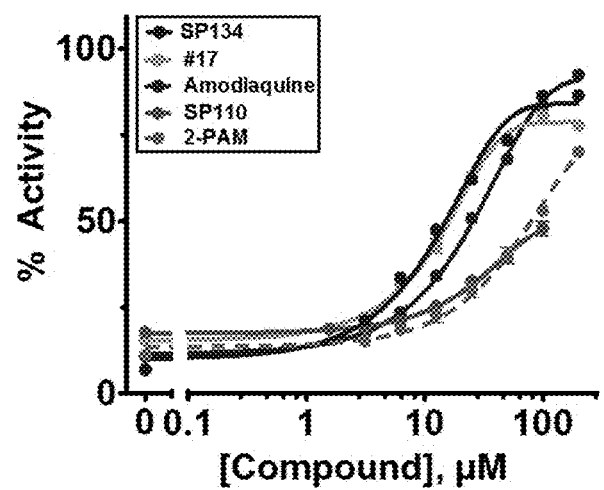
FIG. 28A-28C are a series of line and scatter plots showing reactivation of huBuChE and huAChE.
Figure 28B:
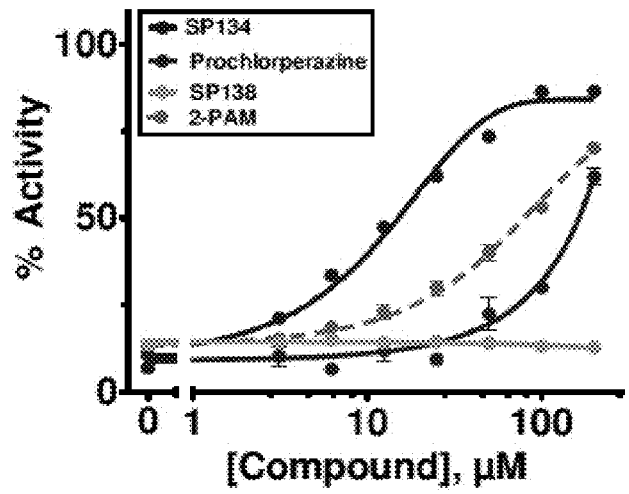
Figure 28C:
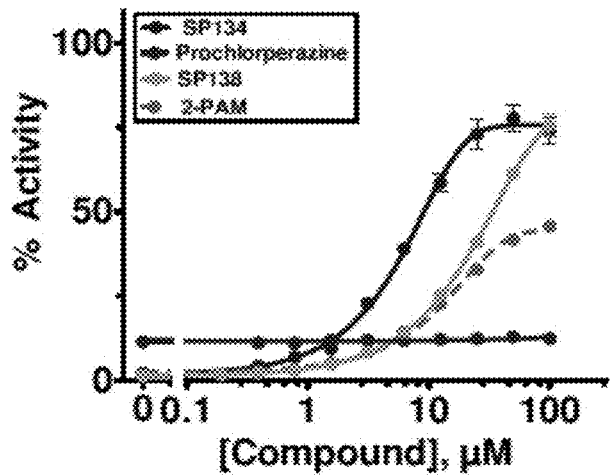

Results showed that SP134 effectively reactivated BuChE (see e.g., FIG. 28A). Results also showed that ADOC and SP138 do not reactivate huBuChE but SP134 does (see e.g., FIGS. 28B-C).

REFERENCES

Prado V F, Roy A, Kolisnyk B, Gros R, Prado M A. Regulation of cholinergic activity by the vesicular acetylcholine transporter. *Biochem J.* 2013 Mar. 1; 450(2): 265-74.

Millard C B, Broomfield C A. Anticholinesterases: medical applications of neurochemical principles. *J Neurochem.* 1995 May; 64(5):1909-18.

Pope C, Karanth S, Liu J. Pharmacology and toxicology of cholinesterase inhibitors: uses and misuses of a common mechanism of action. *Environ Toxicol Pharmacol.* 2005 May; 19(3):433-46.

Kuca K, Juna D, Musilek K. Structural requirements of acetylcholinesterase reactivators. *Mini Rev Med Chem.* 2006 March; 6(3):269-77.

What is claimed is:

1. A method of activating or reactivating an acetylcholinesterase (AChE) comprising:

contacting, in vitro or in vivo, non-activated or inactivated AChE and a compound of Formula (II):

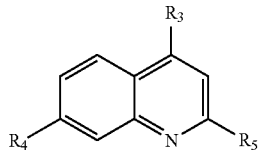

Formula (II)

or a pharmaceutically acceptable salt, including all tautomers and stereoisomers, thereof wherein, $R_3$ represents hydrogen;

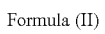

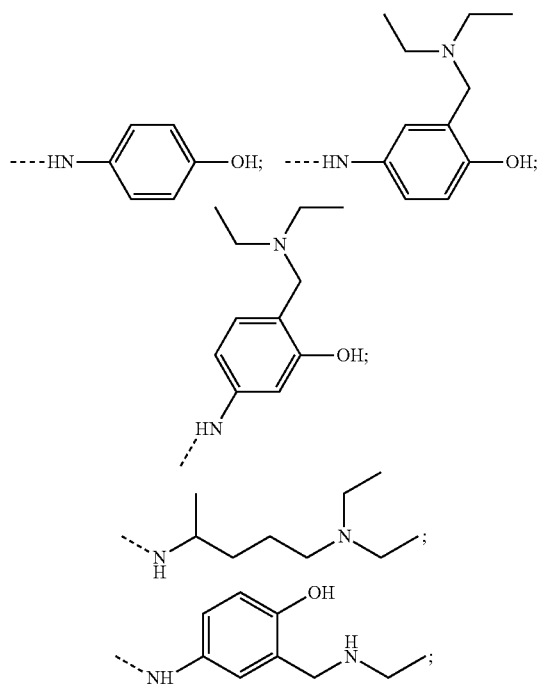

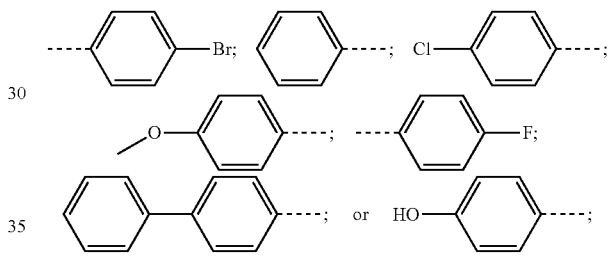

$R_4$ represents hydrogen or chloro; and
$R_5$ represents hydrogen;

wherein the dashed line (- - - - - -) represents a bond to Formula (II).

2. The method of claim 1, wherein the compound is

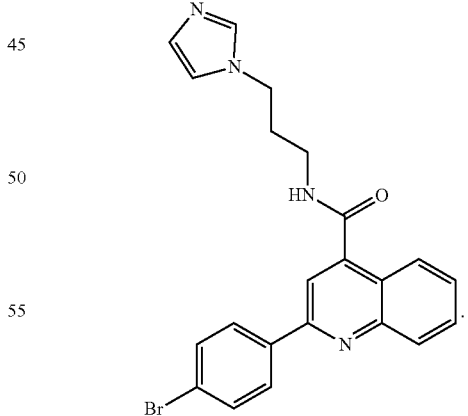

SP138

3. The method of claim 1, wherein the compound further comprises a pharmaceutically acceptable carrier or excipient.

4. A method of activating or reactivating an acetylcholinesterase (AChE) comprising:

contacting, in vitro or in vivo, non-activated or inactivated AChE and a compound of Formula (I):

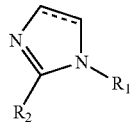

or a pharmaceutically acceptable salt, including all tautomers and stereoisomers, thereof wherein, $R_1$ represents hydrogen;

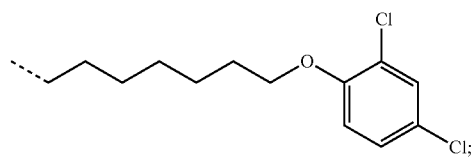

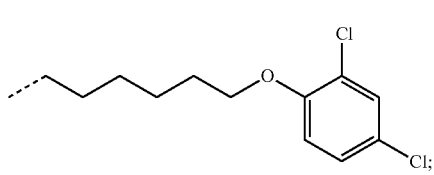

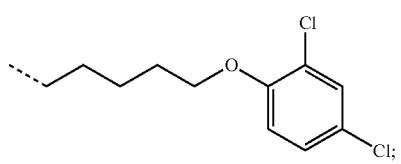

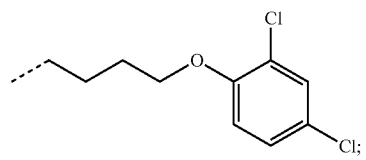

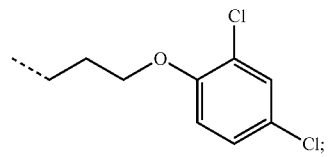

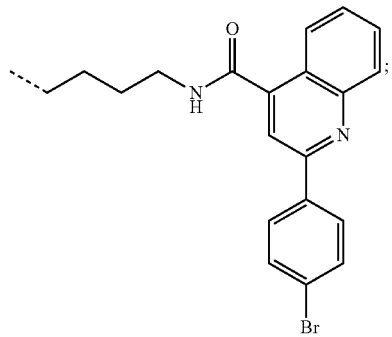

and
$R_2$=hydrogen; or wherein the dashed line (- - - - - -) represents a bond to Formula (I) and the dashed and solid line (- - - - -) of Formula (I) represents a double bond if $R_1$ or $R_2$ is hydrogen and represents a single bond if $R_1$ and $R_2$ are not hydrogen.

5. The method of claim 1, wherein the reactivating comprises reversing inactivation of an acetylcholinesterase.

6. The method of claim 4, wherein the reactivating comprises reversing inactivation of an acetylcholinesterase.

7. The method of claim 4, wherein the compound is
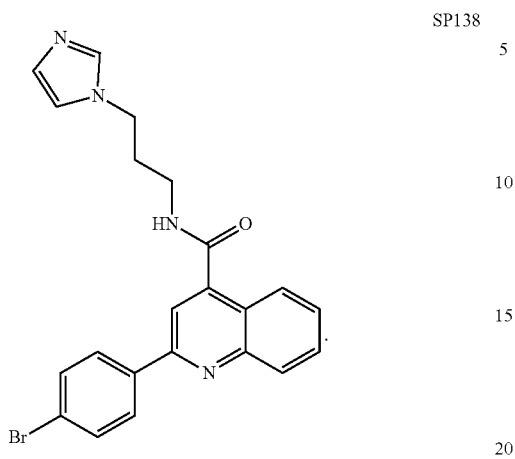
SP138
8. The method of claim 4, wherein the compound further comprises a pharmaceutically acceptable carrier or excipient.
* * * * *